United States Patent
Breitweiser et al.

(10) Patent No.: US 10,888,653 B2
(45) Date of Patent: *Jan. 12, 2021

(54) FEEDING SET WITH CASSETTE AND RELATED METHODS THEREFOR

(71) Applicant: KPR U.S., LLC, Mansfield, MA (US)

(72) Inventors: Kenneth M. Breitweiser, Brighton, IL (US); James M. Harr, Wentzville, MO (US); Joel D. Wiesner, O'Fallon, MO (US)

(73) Assignee: KPR U.S., LLC, Mansfield, MA (US)

( * ) Notice: Subject to any disclaimer, the term of this patent is extended or adjusted under 35 U.S.C. 154(b) by 52 days.

This patent is subject to a terminal disclaimer.

(21) Appl. No.: 16/278,874

(22) Filed: Feb. 19, 2019

(65) Prior Publication Data

US 2019/0240400 A1     Aug. 8, 2019

Related U.S. Application Data

(63) Continuation of application No. 15/234,019, filed on Aug. 11, 2016, now Pat. No. 10,252,000, which is a
(Continued)

(51) Int. Cl.
| | |
|---|---|
| *A61M 5/142* | (2006.01) |
| *F04B 43/12* | (2006.01) |
| *A61M 5/168* | (2006.01) |
| *F04B 43/00* | (2006.01) |
| *F04B 43/08* | (2006.01) |

(52) U.S. Cl.
CPC .... *A61M 5/14232* (2013.01); *A61M 5/16804* (2013.01); *A61M 5/16831* (2013.01); *F04B 43/0072* (2013.01); *F04B 43/082* (2013.01); *F04B 43/12* (2013.01); *F04B 43/1223* (2013.01); *F04B 43/1253* (2013.01);
(Continued)

(58) Field of Classification Search
None
See application file for complete search history.

(56) References Cited

U.S. PATENT DOCUMENTS

| | | | |
|---|---|---|---|
| 3,353,491 A * | 11/1967 | Bastian | F04B 43/1284 417/477.9 |
| 3,597,124 A * | 8/1971 | Adams | F04B 43/1284 417/477.11 |

(Continued)

FOREIGN PATENT DOCUMENTS

| | | |
|---|---|---|
| CN | 87107936 A | 7/1988 |
| CN | 1973132 A | 5/2007 |

(Continued)

*Primary Examiner* — Jenna Zhang
(74) *Attorney, Agent, or Firm* — Arent Fox LLP

(57) ABSTRACT

A pump set for use with a pumping apparatus having a rotor with a plurality of rollers mounted on the rotor rotatable about an axis of rotation is disclosed. The pump set comprises a cassette body comprising a stator member with a fixed portion secured to the cassette body, a second portion opposite the fixed portion, a reaction surface and a second surface opposite the reaction surface, the reaction surface defined between the fixed portion and the second portion, and a tube secured to the cassette body, at least a portion of the tube is disposed against the reaction surface.

14 Claims, 19 Drawing Sheets

Related U.S. Application Data continuation of application No. 14/021,567, filed on Sep. 9, 2013, now Pat. No. 9,421,322.

(60) Provisional application No. 61/726,283, filed on Nov. 14, 2012.

(52) U.S. Cl.
CPC ..... *F04B 43/1269* (2013.01); *A61M 2205/12* (2013.01); *A61M 2205/3317* (2013.01)

(56) References Cited

U.S. PATENT DOCUMENTS

| | | | |
|---|---|---|---|
| 4,138,205 A * | 2/1979 | Wallach | F04B 43/1284 417/360 |
| 4,545,744 A | 10/1985 | Weber et al. | |
| 4,558,996 A * | 12/1985 | Becker | F04B 43/1253 417/374 |
| 4,559,040 A * | 12/1985 | Horres | F04B 43/123 417/474 |
| 4,650,471 A | 3/1987 | Tamari | |
| 4,666,598 A | 5/1987 | Heath et al. | |
| 4,886,431 A * | 12/1989 | Soderquist | F04B 43/1292 417/477.2 |
| 4,976,590 A | 12/1990 | Baldwin | |
| 5,096,393 A * | 3/1992 | Van Steenderen | F04B 43/1292 417/475 |
| 5,256,041 A | 10/1993 | Tucker | |
| 5,413,252 A * | 5/1995 | Magnus | B67D 1/108 222/129.1 |
| 5,470,211 A * | 11/1995 | Knott | F04B 43/1253 417/477.11 |
| 5,655,897 A | 8/1997 | Neftel et al. | |
| 5,927,956 A * | 7/1999 | Lim | A61M 3/0258 417/477.13 |
| 5,971,726 A | 10/1999 | Yoshida et al. | |
| 6,027,459 A | 2/2000 | Shain et al. | |
| 6,062,829 A | 5/2000 | Ognier | |
| D437,058 S | 1/2001 | Gozani | |
| D456,509 S | 4/2002 | Schultz | |
| 6,419,466 B1 * | 7/2002 | Lowe | A47J 31/402 417/417 |
| D479,325 S | 9/2003 | Tyce | |
| 6,736,617 B2 | 5/2004 | Domroese | |
| 7,092,797 B2 | 8/2006 | Gaines et al. | |
| 7,214,038 B2 * | 5/2007 | Saxer | F04B 43/1253 417/477.2 |
| D562,985 S | 2/2008 | Brefka et al. | |
| 7,374,545 B2 | 5/2008 | Alroy | |
| 7,534,099 B2 | 5/2009 | Knauper et al. | |
| 7,608,059 B2 | 10/2009 | Harr et al. | |
| D603,968 S | 11/2009 | Brefka | |
| 7,722,338 B2 * | 5/2010 | Nordell | F04B 43/1253 417/477.11 |
| 7,934,912 B2 | 5/2011 | Voltenburg, Jr. et al. | |
| 8,043,077 B2 | 10/2011 | Miyazaki et al. | |
| 8,047,819 B2 | 11/2011 | Lawrence et al. | |
| 8,128,382 B2 | 3/2012 | Smits | |
| 8,197,236 B2 | 6/2012 | McIntosh | |
| D664,258 S | 7/2012 | Harkin et al. | |
| 8,262,616 B2 | 9/2012 | Grant et al. | |
| 8,353,683 B2 | 1/2013 | Miyazaki et al. | |
| 8,545,198 B2 | 10/2013 | Artsyukhovich et al. | |
| 8,550,310 B2 | 10/2013 | Alstad et al. | |
| D697,626 S | 1/2014 | Laplante et al. | |
| D715,924 S | 10/2014 | Green | |
| 2002/0131881 A1 | 9/2002 | Kagawa et al. | |
| 2005/0069436 A1 | 3/2005 | Shibasaki | |
| 2006/0067845 A1 | 3/2006 | Kojima et al. | |
| 2007/0217932 A1 * | 9/2007 | Voyeux | F04B 43/1284 417/477.2 |
| 2008/0112828 A1 | 5/2008 | Muri et al. | |
| 2009/0053085 A1 * | 2/2009 | Thompson | F04B 43/1253 417/477.2 |
| 2010/0129247 A1 | 5/2010 | Lauer | |
| 2010/0129248 A1 * | 5/2010 | Mou | F04B 43/1284 417/477.9 |
| 2010/0301071 A1 * | 12/2010 | Alstad | F04B 43/1269 222/214 |
| 2011/0286870 A1 | 11/2011 | Bach | |
| 2011/0313358 A1 | 12/2011 | Hariharesan et al. | |
| 2012/0034117 A1 | 2/2012 | Pfouts et al. | |
| 2012/0083735 A1 | 4/2012 | Pfouts | |
| 2012/0130309 A1 | 5/2012 | Hariharesan et al. | |
| 2012/0143151 A1 | 6/2012 | Low et al. | |
| 2012/0195777 A1 | 8/2012 | Stejskal et al. | |
| 2013/0071272 A1 * | 3/2013 | Juretich | A61M 5/14232 417/477.2 |
| 2013/0280104 A1 | 10/2013 | Heide et al. | |
| 2014/0135731 A1 | 5/2014 | Breitweiser et al. | |

FOREIGN PATENT DOCUMENTS

| | | |
|---|---|---|
| EP | 0570259 A1 | 11/1993 |
| EP | 1769815 A1 | 4/2007 |
| FR | 2598182 A1 | 11/1987 |

* cited by examiner

FEEDING SET WITH CASSETTE AND RELATED METHODS THEREFOR

CROSS-REFERENCE TO RELATED APPLICATION

This application is a continuation of U.S. Ser. No. 15/234,019, filed Aug. 11, 2016, which is a continuation of U.S. Ser. No. 14/021,567, filed Sep. 9, 2013 which claims the benefit of priority under 35 U.S.C. § 119 to U.S. Patent Application No. 61/726,283, titled CASSETTE FEEDING SET AND RELATED METHODS THEREFOR, which was filed on Nov. 14, 2012, the entire contents of all of which are incorporated herein by reference in its their entirety for all purposes.

FIELD OF THE INVENTION

The present invention generally relates to a flow control system with a flow control apparatus and a feeding set, and more particularly to a cassette for use with the flow control apparatus.

BACKGROUND OF THE INVENTION

Delivering fluids by utilizing peristaltic pumps is known. For example, administering medicine or nutrition to a patient can be effected by utilizing peristaltic flow control systems. Typically in such systems, fluid is delivered to the patient by a pump set including a flexible elastomeric tubing loaded on a flow control apparatus, such as a peristaltic pump, which delivers fluid to the patient at a controlled rate of delivery. The peristaltic pump usually has a housing that includes a rotor operatively engaged to at least one motor through a gearbox. The rotor drives fluid through the flexible tubing of the pump set by the peristaltic action effected by reversible compression created by impingement, e.g., pinching, by one or more rollers that translate by rotation of the rotor. One or more motors operatively connected to a rotatable shaft drive the rotor, which in turn progressively compresses the elastomeric tubing that drives the fluid at a controlled rate. The pump set may have a valve mechanism for permitting or preventing fluid flow communication through the pump set. The flow control system may also have a controller that operatively regulates the one or more motors which effectively controls fluid flow.

Peristaltic pumps operate by delivering fluid in small charges called "aliquots". The rotor engages elastomeric tubing of the pump set, pinching off a portion of the elastomeric tubing and pushing fluid forward of the pinch point, e.g., closer to the patient than to the source of fluid toward the patient. Typically, the volume of fluid to be administered to the patient is controlled in the pump by counting the number of aliquots, each being of substantially the same volume, and stopping when the number reaches an amount corresponding to the total desired volume of fluid to be delivered. Peristaltic pumps are sanitary and generally accurate and therefore very useful in the administration of medication and therapeutic fluids to the patient. However, the accuracy of the pump may be dependent upon the dimensional stability of the elastomeric tubing of the pump set. Further, continued operation of the tubing of the pump set can causing the volume of each aliquot to vary because of the effect of such deformation. As a result, the accuracy of the volumes delivered to the patient can be compromised.

SUMMARY OF THE INVENTION

One or more aspects of the invention can be directed to a cassette for use with a pumping apparatus having a pumping system including a rotor and at least one roller mounted on the rotor for engaging a pump set. The cassette can further comprise a tube permanently or releasably attachable to the cassette body and defining at least a portion of the pump set. At least a portion of the elastomeric tube can be looped around the rotor forming a U-shaped configuration when the cassette is engaged to the pumping apparatus. The cassette can comprise a cassette body configured for receiving the pump set and releasable attachment to the pumping apparatus to mount the pump set on the pumping apparatus for engagement by the at least one roller to deliver fluid through the pump set, and a flexible stator member, such as a flexible cantilever member, on the cassette body positioned generally opposite the rotor when the cassette is attached to the pumping apparatus to support an elastomeric tubing of the pump set when engaged by the roller; the flexible stator member being adapted to float relative to the cassette body so that when the roller engages the pump set elastomeric tubing, the flexible stator member moves away or deflects from the roller which is believed to at least partially reduce tension in the tubing. The flexible stator member can be integrally formed with the cassette body; and in some cases, the flexible stator member can be a separate component attached to the cassette body. The flexible stator member typically has a length extending along an arc, wherein the flexible stator member has a first thickness extending along the entire length thereof and a second thickness different from the first thickness extending along the entire length of the flexible stator member. The cassette can further comprise a stop member opposing the flexible stator member for limiting movement of the flexible stator member away from the rotor. Typically, the stop member has a width that is greater than a width of the flexible stator member. The stop member is typically formed integrally with the cassette body. The cassette can further comprise one or more raised projections, such as tabs, mounted on the stop member for engagement with one or more notches on the pumping apparatus to locate or positively position the cassette on the pumping apparatus. The one or more projections can be at a bottom of the cassette body. The cassette can further comprise a tab extending generally from a top of the cassette body for engaging a catch on the pumping apparatus to securely attach and engage the cassette to the pumping apparatus. The cassette can further comprise guides therein for positioning the elastomeric tubing within the cassette body; each guide can form or define a tapered channel that receives at least a portion of the tube of the pump set. One or more further aspects of the invention can be directed to the cassette in combination with the pump set.

One or more aspects of the invention can be directed to a pump set for use with a pumping apparatus having a pumping system including a rotor for rotation about a pump axis and at least one roller mounted on the rotor for engaging a pump set to deliver fluid through the pump set to a subject. The pump set can comprise a resiliently deformable tube for carrying a liquid, such as a nutritional liquid or a medical liquid, and a cassette receiving the tube and adapted for releasable attachment to the pumping apparatus to mount the pump set on the pumping apparatus for engagement of the tubing with the at least one roller to deliver the liquid therethrough, wherein the cassette comprises a deflectable platen or a flexible stator surface arranged to be generally perpendicular to the pump axis and in generally opposed relation to said at least one roller to act as a reaction surface against which the tube is squeezed by the rotor, and wherein the pump set is configured so that upon mounting the pump set on the pumping apparatus, the tube is generally not longitudinally stretched and not in longitudinally tension, or is longitudinally stretched by a negligible amount. The tube typically has a central flow passage that lies generally in a plane within the cassette, and the flexible stator surface of the cassette is arranged parallel to the plane of the central flow passage within the cassette. In some cases, the flexible stator surface is generally planar. In further cases, the tube is contained entirely within the cassette.

One or more aspects of the invention can be directed to a pumping apparatus for use with a pump set to deliver fluid through the pump set. The pumping apparatus can comprise a housing capable of receiving at least a portion of the pump set, and a pumping device mounted in the housing and configured to act on the pump set to produce fluid flow in the pump set when the pump set is received by the housing; the pumping device can comprise a rotor having an axis of rotation and at least one roller mounted on the rotor for engaging the pump set to move fluid though the pump set; the roller can have an axis of rotation perpendicular to the axis of rotation of the rotor. The pumping apparatus can further comprise a plurality of rollers mounted on the rotor, each roller having an axis of rotation perpendicular to the axis of rotation of the rotor. Some further aspects of the invention can pertain to the pumping apparatus in combination with a pump set including a cassette comprising a flexible stator having a planar stator surface. The stator surface can extend in a plane that extends perpendicular to the axis of rotation of the rotor.

One or more further aspects of the invention can be directed to a pump set for use with a pumping apparatus having a rotor with a plurality of rollers mounted on the rotor rotatable about an axis of rotation, the pump set comprising a cassette body comprising a flexible stator member with a fixed portion secured to the cassette body, a second portion opposite the fixed portion, a reaction surface and a second surface opposite the reaction surface, the reaction surface defined between the fixed portion and the second portion; and a tube secured to the cassette body, at least a portion of the tube is disposed against the reaction surface. The stator member, in some cases, is cantilevered at the fixed portion and unfixed at the second portion which can provide the reaction surface with a deflection displacement. The pump set can further comprise a stop member constructed and arranged, e.g., sized and positioned, to limit the translation of the stator member to a predetermined or target deflection displacement. At least a portion of the reaction surface, in some cases, defines an arcuate surface with a center of curvature that is at least partially coincident with the axis of rotation. In other cases, the arcuate surface has a curvature that is offset relative to the axis of rotation. The tube, in still further cases, can be contained within the cassette body. The stator member can further comprise a flange on the second surface, wherein the flange extends along at least a portion of the second surface between the first end and the second end.

One or more aspects of the invention can pertain to a method of facilitating use of a pumping apparatus having a rotor with a plurality of rollers, wherein the method comprises providing a cassette body comprising a flexible stator member with a fixed portion secured to the cassette body, a second portion opposite the fixed portion, a reaction surface and a second surface opposite the reaction surface, the reaction surface defined between the fixed portion and the second portion, and securing a tube to the cassette body with at least a portion of the tube is disposed against the reaction surface.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

One or more aspects of the present invention pertain to peristaltic pumps such as rotary peristaltic pumps and particularly to rotary peristaltic pumps utilizing a flexible stator. Any one or more advantageous features or structures that provide or facilitate any one or more of such feature may be implemented in a peristaltic pumps employed in various commercial and industrial applications. Thus, although the detailed discussion is directed to an enteral feed pump with a cassette, any one or more features of the invention may be embodied or implemented in other peristaltic pumps, with or without a cassette assembly. For example, although the exemplarily discussed pump is a rotary peristaltic enteral feeding pump, the present invention has application to other types of peristaltic pumps (not shown), including medical infusion pumps. The general construction and operation of the enteral feeding pump, except as set forth hereinafter, may be generally the same as disclosed in co-assigned U.S. Pat. No. 7,608,059 filed May 24, 2004, entitled FLOW CONTROL APPARATUS; U.S. Pat. No. 7,092,797 filed May 25, 2004, entitled FLOW MONITORING SYSTEM FOR A FLOW CONTROL APPARATUS; and U.S. Pat. No. 7,534,099 filed Sep. 30, 2005, entitled ALIQUOT CORRECTION FOR FEEDING SET DEGRADATION, each of which is incorporated herein by reference. One or more of the various features and aspects of the invention may be implemented in peristaltic pumps that use mechanisms other than rollers without departing from the scope of the present invention such as linear peristaltic pumps. Moreover, although an exemplary feeding set 7 is shown, other types of pump sets (not shown) can be used without departing from the scope of the present invention.

Figure 1:
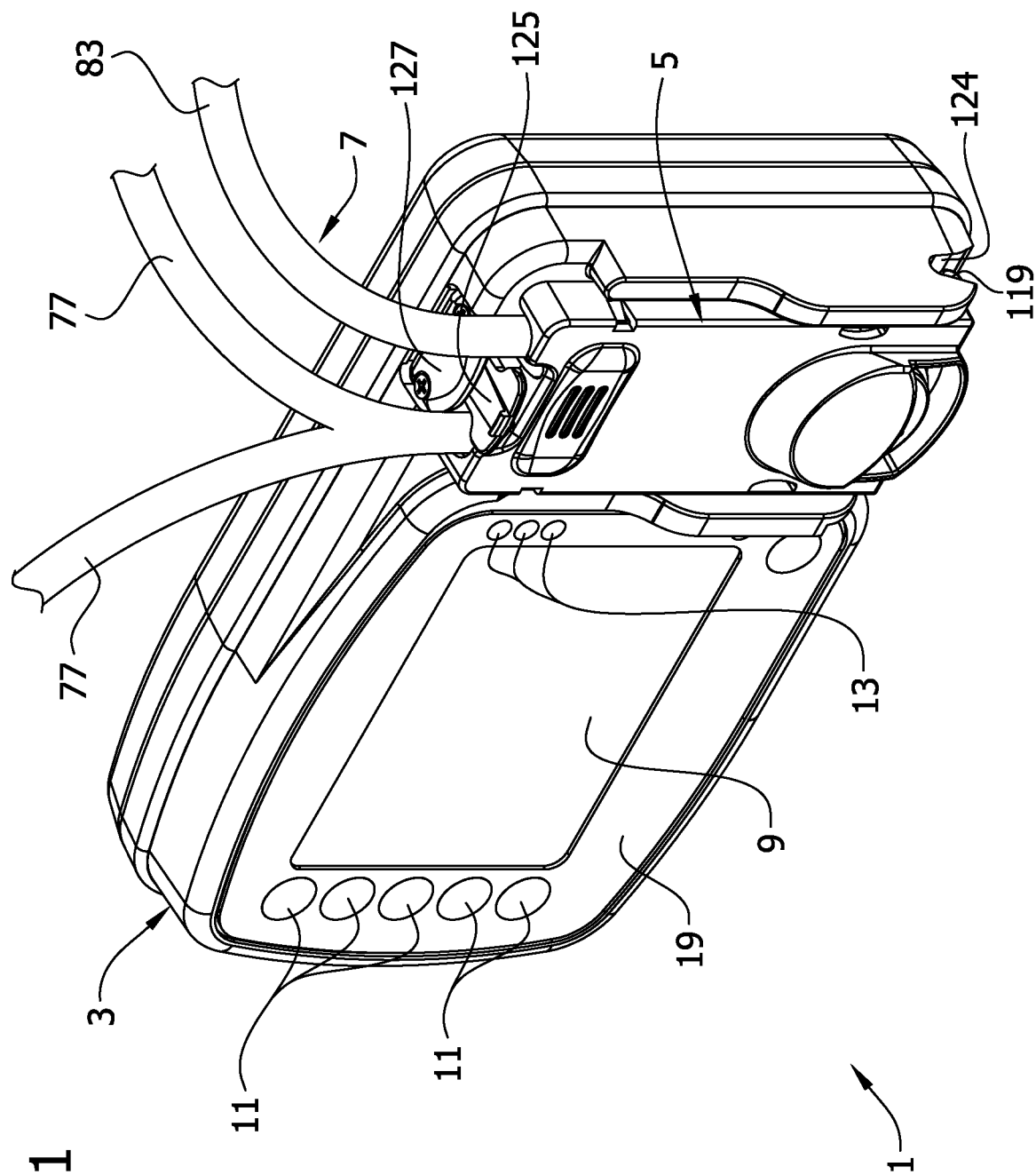
FIG. 1 is a perspective view of an feeding system with pumping apparatus and a fragmentary portion of a feeding set and a cassette, in accordance with one or more embodiments of the present invention.
Figure 2:
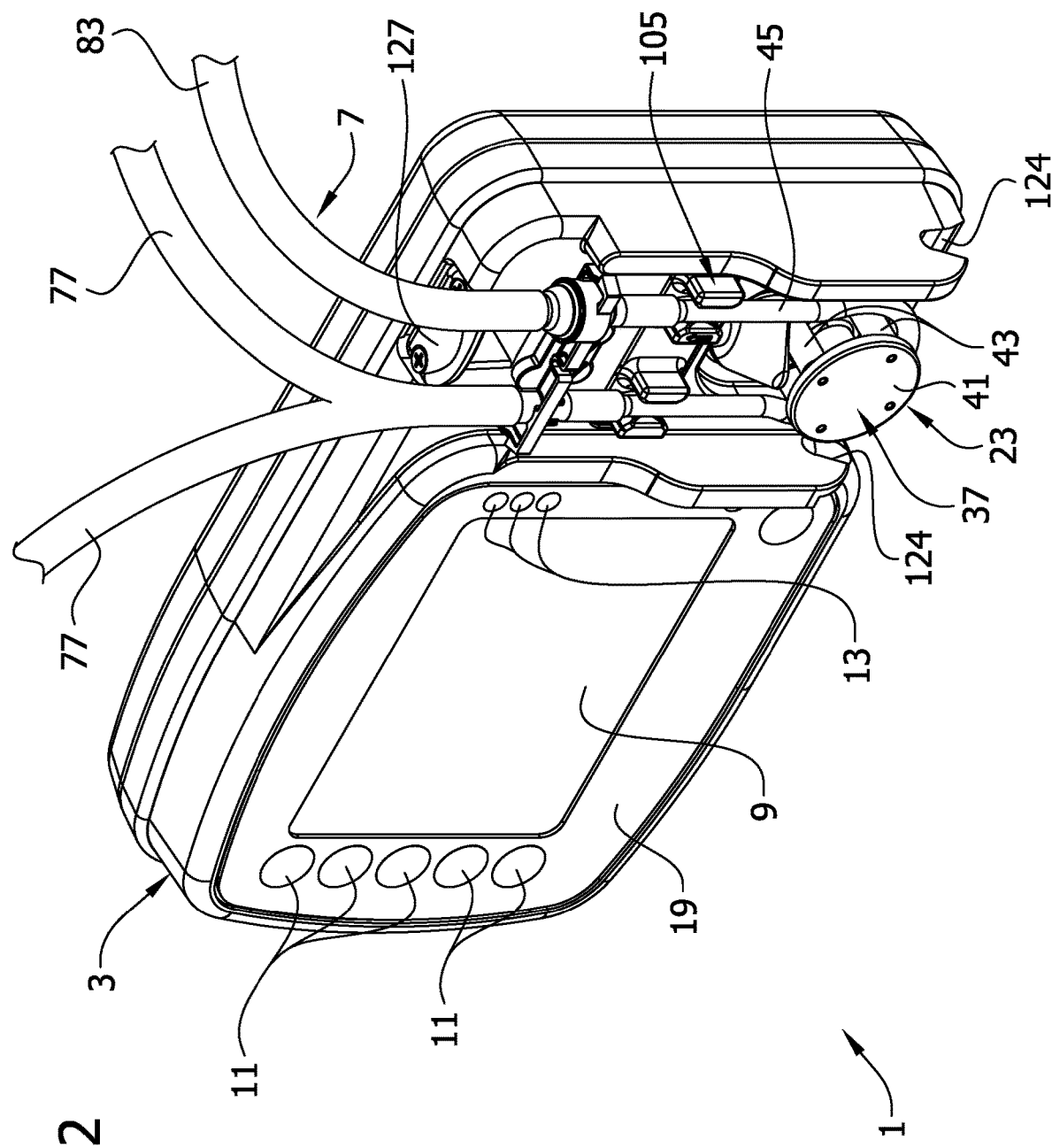
FIG. 2 is a perspective view of the system of FIG. 1 a fragmentary portion of a feeding set with the cassette removed.
Figure 3:
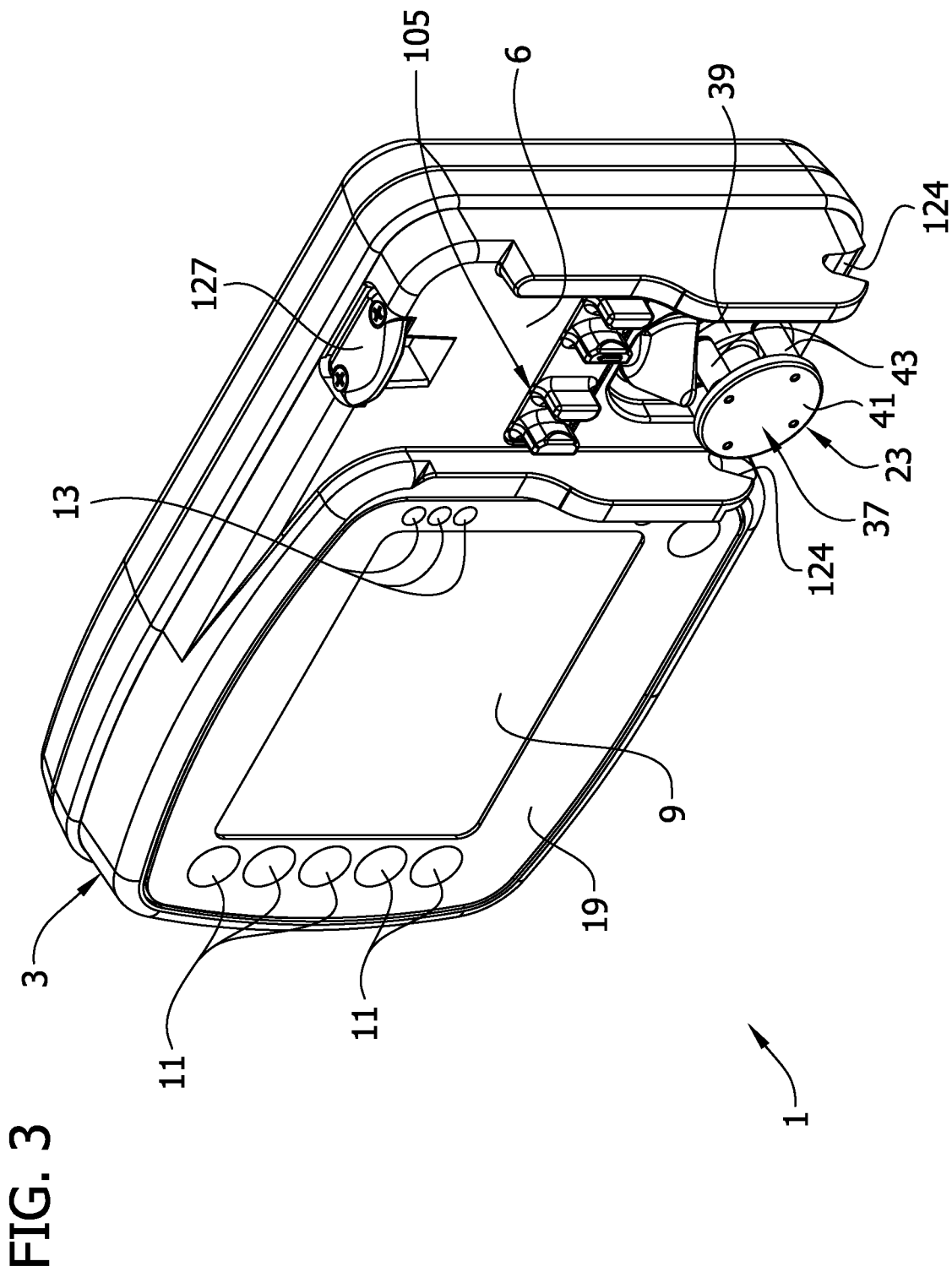
FIG. 3 is the perspective view of FIG. 1 without the feeding set.

Referring now to the drawings, and in particular FIGS. 1-3, an exemplary enteral feeding pump (broadly, "pumping apparatus") constructed according to the any one or more of the principles of the present invention is generally indicated at 1. The feeding pump may comprise a housing generally indicated at 3 that is constructed so as to mount a cassette, generally indicated at 5, and a feeding set (broadly, a "pump set"), a fragmentary portion generally indicated at 7, removably received in the cassette. The cassette 5 is releaseably attachable to the housing 3. In the illustrated embodiment, the cassette 5 is removably received in a cassette recess 6 in the housing 3 (FIG. 3). It will be appreciated that "housing" as used herein may include many forms of supporting structures (not shown), including without limitation multipart structures and structures that do not enclose or house the working components of the pump 1. The pump 1 may also have one or more display screens 9 on the housing 3 that is capable of displaying information about the status and operation of the pump. Moreover, various aspects and features of the present invention can be implemented without the recess 6. One or more buttons 11 which can be proximate the display screen 9 can be provided for use in controlling and obtaining information from the pump 1, and one or more light emitting diodes 13 can provide status information for the pump. Legs (not shown) may be disposed at the bottom of the housing 3 to support the housing so that the display screen 9 is angled slightly upward for ease of viewing by a user or operator.

The display screen 9 may be part of a front panel (generally indicated at 19) of the housing 3 and may be removably attached to the housing. The enteral feeding pump may further include a pumping unit indicated generally at 23 comprising a pump motor (not shown) connected to a rotor shaft (not shown). A battery (not shown) may be received in the housing 3 for powering the pump motor. A power source other than or in addition to the battery could be used to energize the pump including one or more prime movers which drives the pumping unit through the rotor shaft.

The pumping unit 23 can have a rotor (generally indicated at 37) which can be coupled to the rotor shaft. The rotor 37 may include an inner disk 39, an outer disk 41, and four rollers 43 (only one of which is shown) mounted between the inner and outer disks for rotation relative to the disks about their longitudinal axes (FIGS. 2 and 3). The rollers 43 engage a tube 45 (FIG. 2) of the feeding set 7 to deliver fluid through the feeding set to a subject when the feeding set is received in the cassette 5 and the cassette is attached to the housing 3.

Referring to FIGS. 4-7, the cassette 5 may comprise a cassette body 51 having a front 53, a back 55, a top 57, and a bottom 59. Side walls 61 and top wall 63 may extend from the back 55 of the cassette body 51 forming a back cavity configured for receiving a fitting 65. The tube 45 may be releasably attached to the fitting 65. The fitting 65 may have tabs that allow the fitting 65 to be secured or snapped into the cassette. In some cases, the fitting can be removably secured to the cassette.

Figure 10:
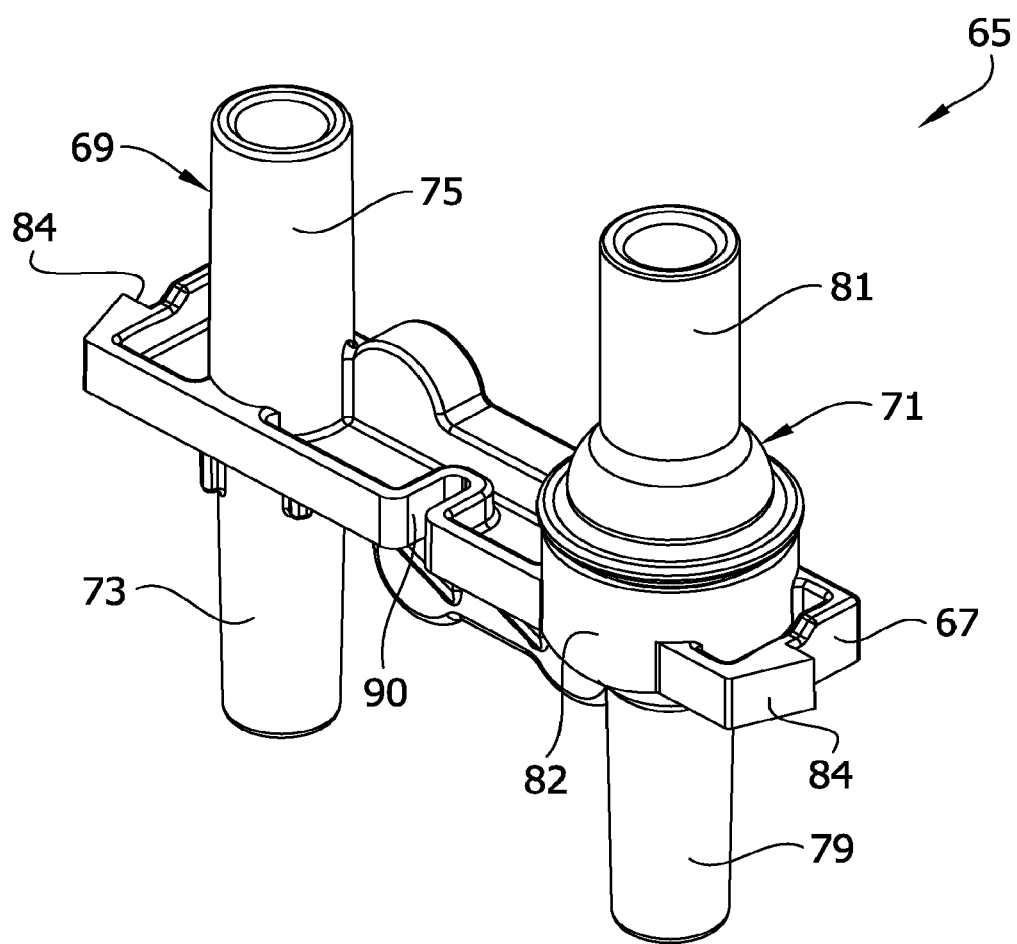
FIG. 10 is a perspective view of the fitting.
Figure 11:
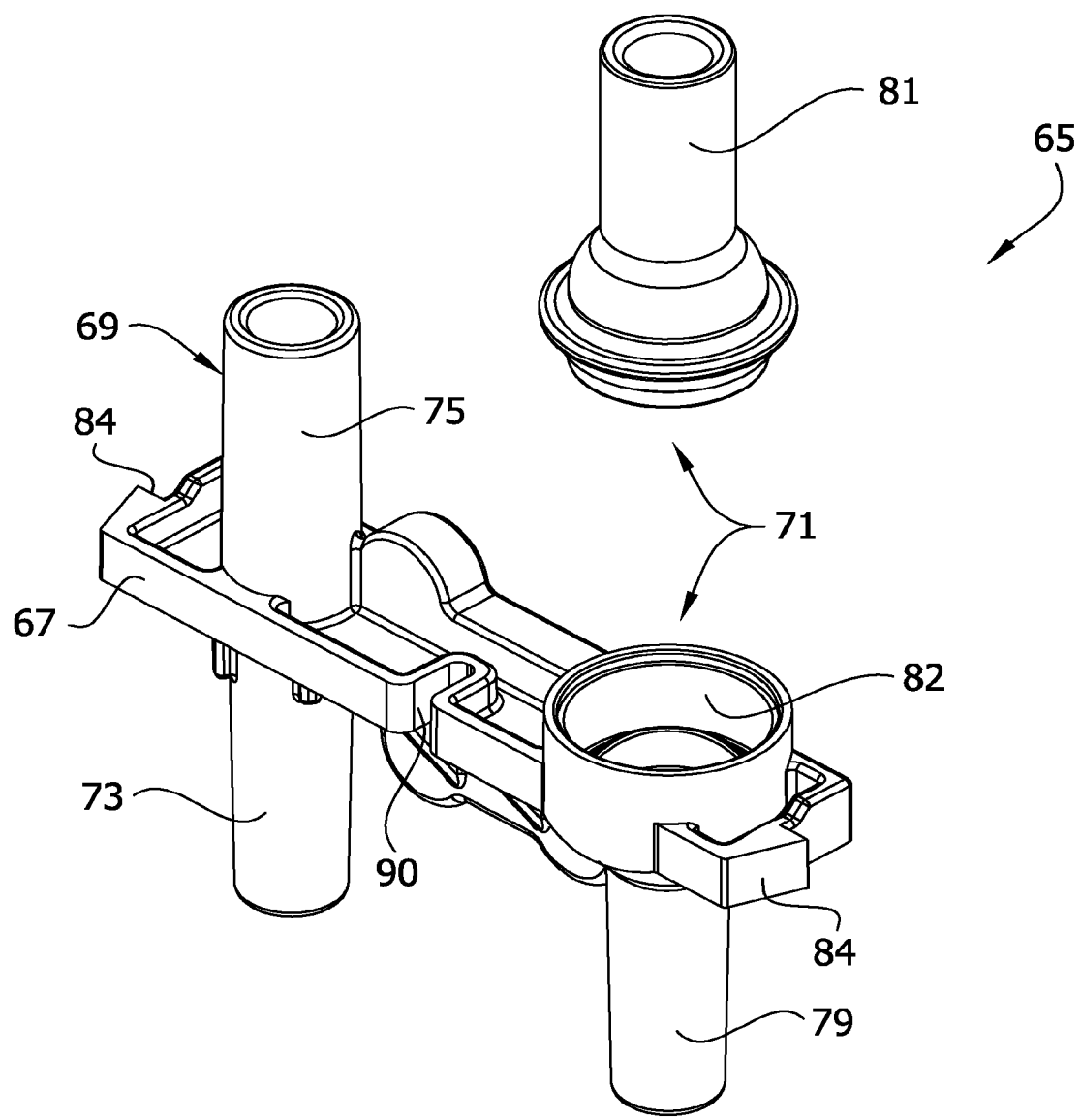
FIG. 11 is an exploded view of the fitting.
Figure 12:
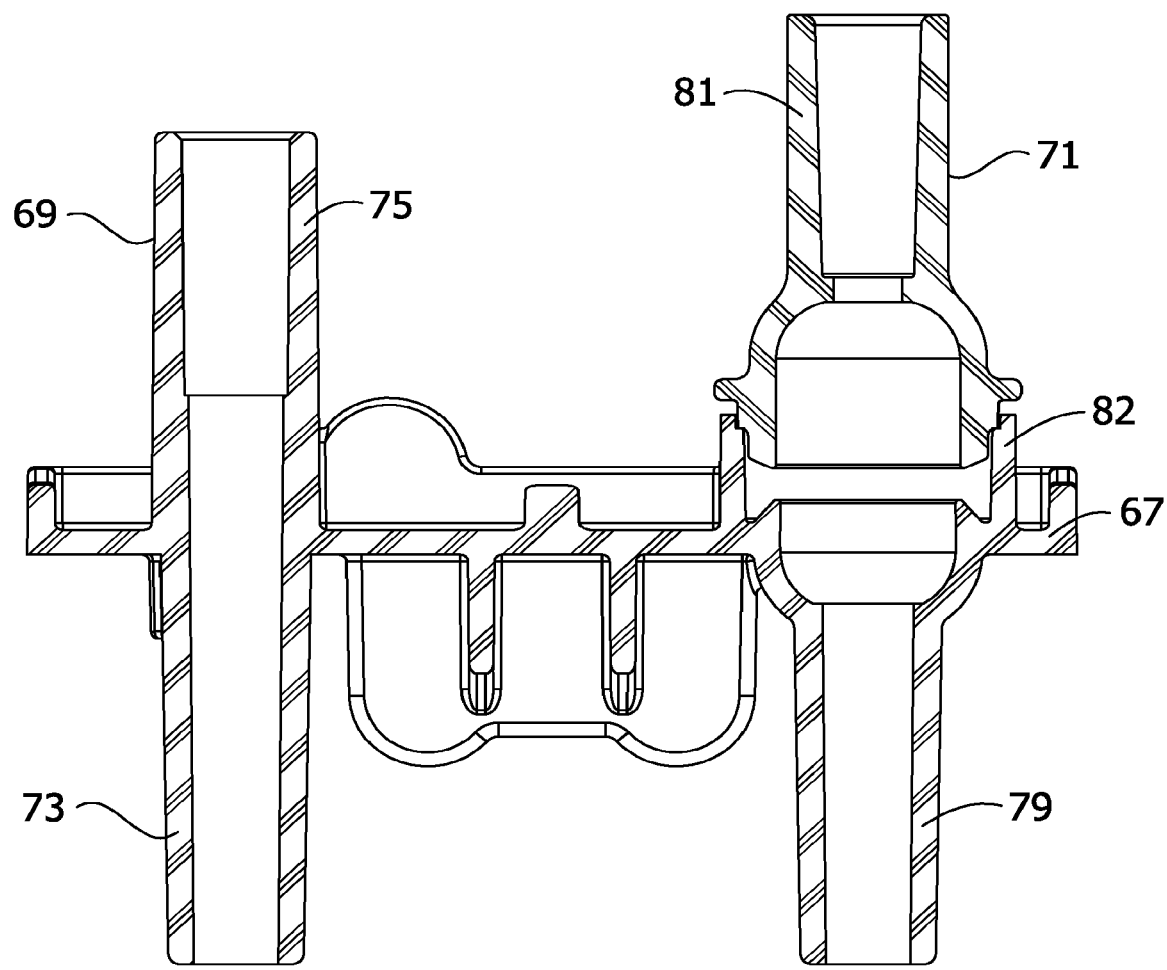
FIG. 12 is a cross-sectional view of the fitting.

The fitting may be a tube holder and can comprise a base 67, an inlet port 69, and an outlet port 71 (FIGS. 10-12). The inlet port 69 may include a first attachment portion 73 for insertion into an inlet end of the tube 45, and a second attachment portion 75 for receiving inlet tubing 77 (FIG. 2). The outlet port 71 may include a first attachment portion 79 for engagement or attachment to, such as by insertion into an outlet end of the tube 45, and a second attachment portion 81 for attachment to such as by receiving outlet tubing 83. The second attachment portion 81 may be removable in a receptacle 82 on the base 67. Alternatively, the second attachment portion 81 can be fixed to the base 67 like the construction of the second attachment portion 75 of the inlet port 69.

The tube 45, inlet tubing 77, and outlet tubing 83 may comprise the pump set 7. It is also envisioned that the cassette 5 may be considered to be part of the pump set. In a preferred embodiment, the cassette 5 is made from a polymeric material such as polycarbonate.

As exemplarily illustrated, tabs 84 can extend from lateral sides of the base 67 and can be configured to be received in respective openings 86 in the sidewalls 61 and front 53 of the cassette 5 to releasably attach the fitting 65 to the cassette. A pair of guide ramps 91 in the side walls 61 may funnel toward the openings 86. The tabs 84 on the fitting 65 can ride along the ramps 91 and be received in the openings 86 to retain the fitting to the cassette body 51. Alternatively, the fitting 65 may be formed integrally with the cassette body 51, or omitted.

Figure 5:
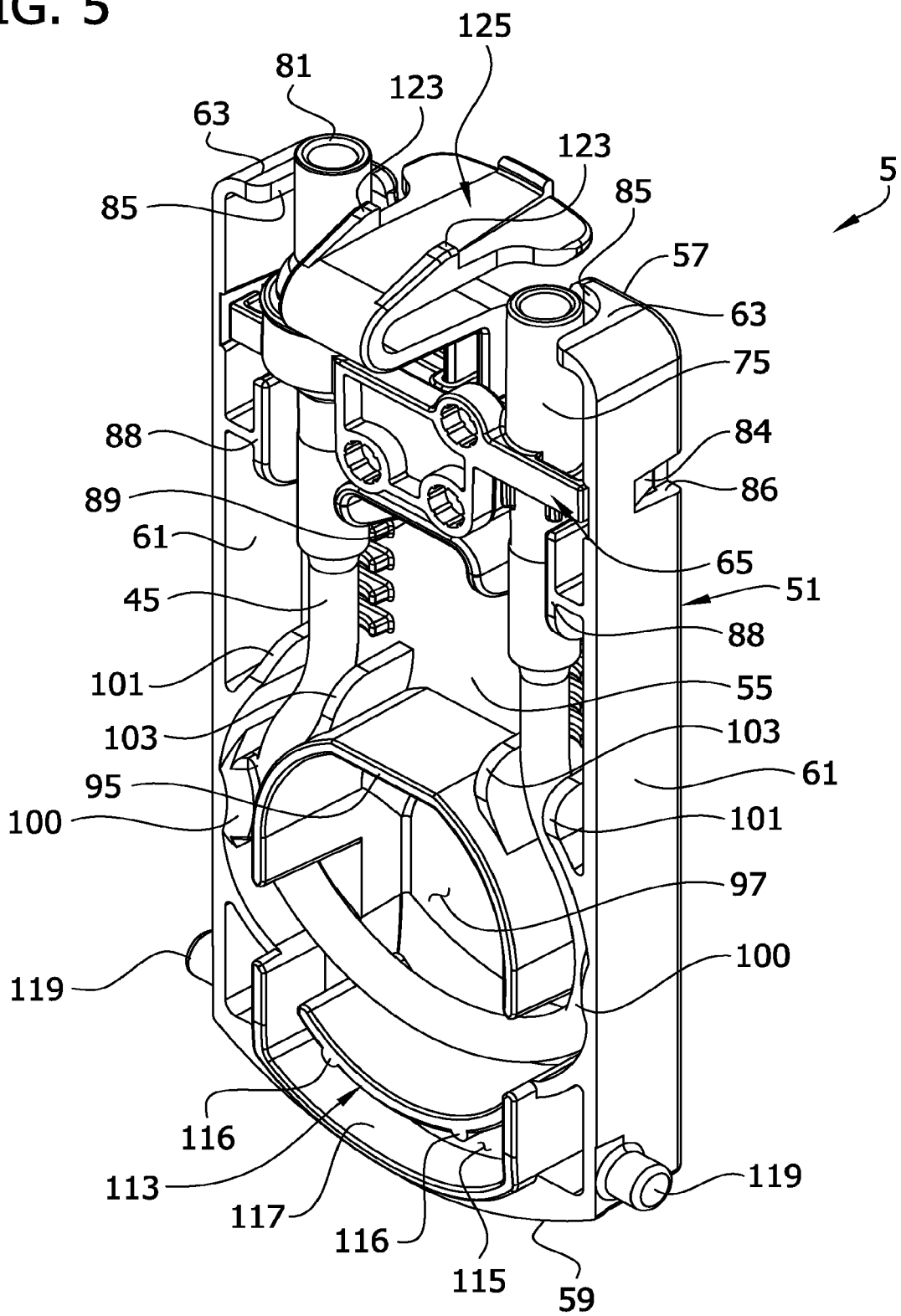
FIG. 5 is a rear perspective view of the cassette.
Figure 6:
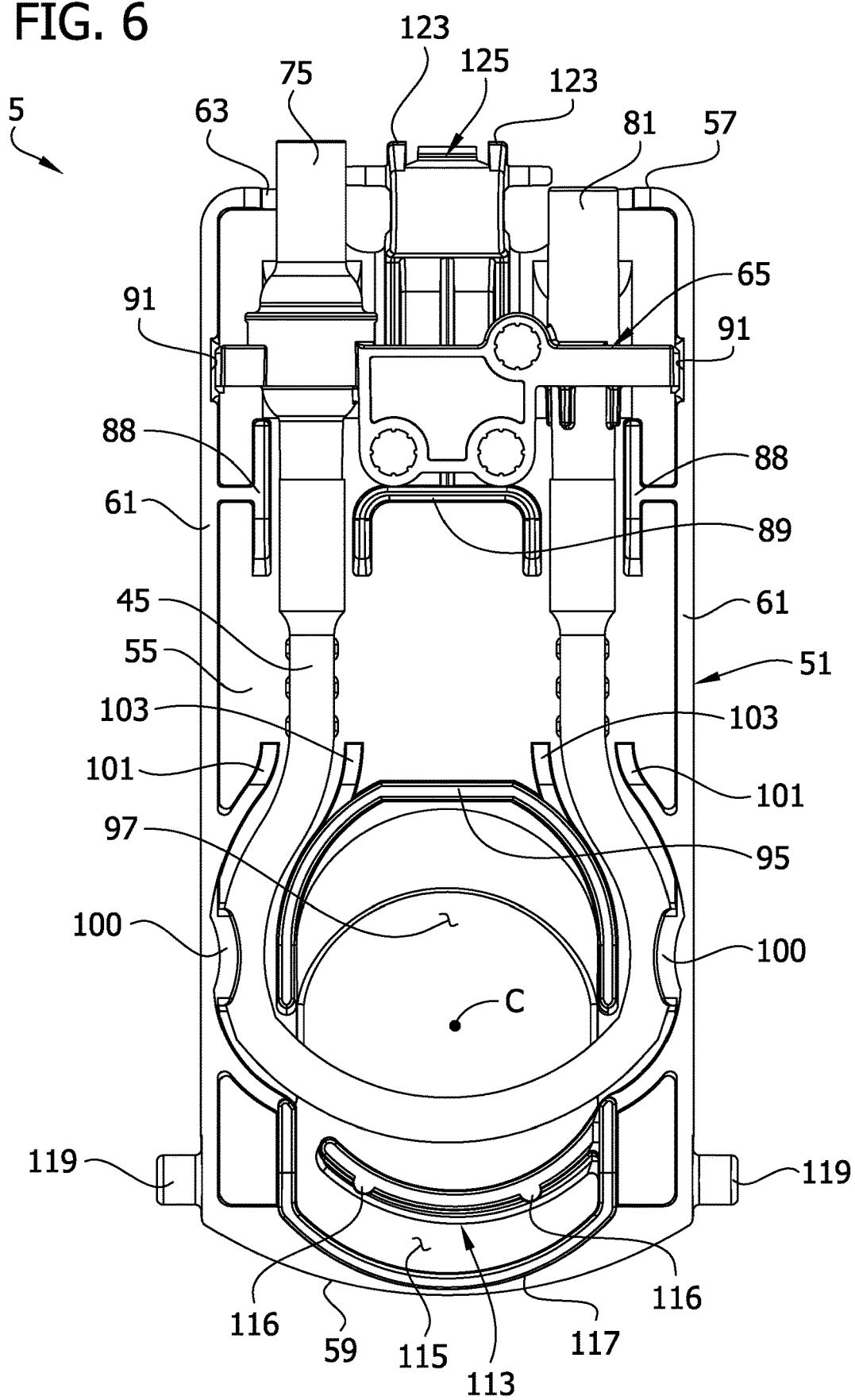
FIG. 6 is a rear elevation view of the cassette.
Figure 7:
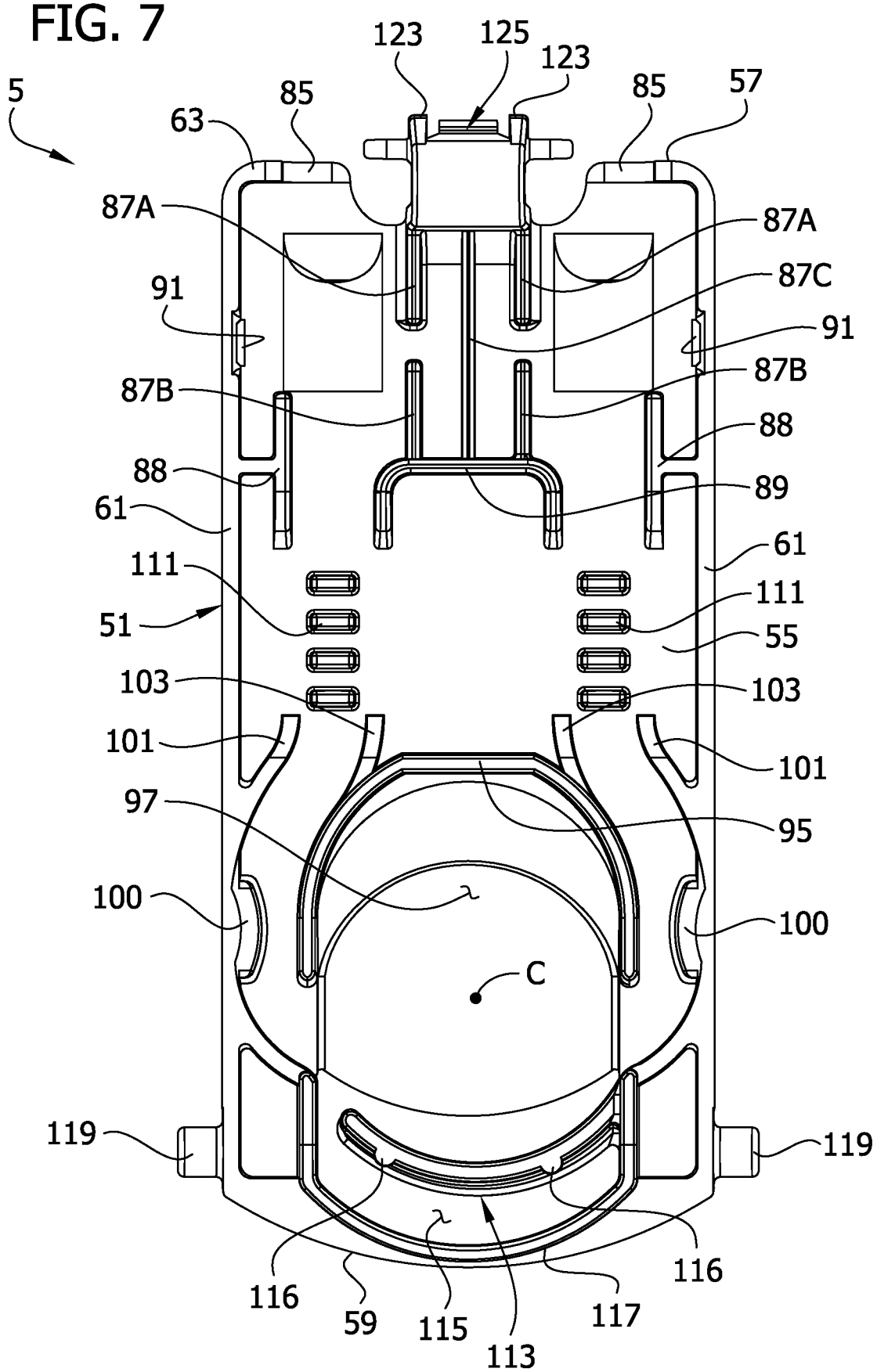
FIG. 7 is the rear elevation view of the cassette of FIG. 6 with a tube and a fitting removed from the cassette.
Figure 8:
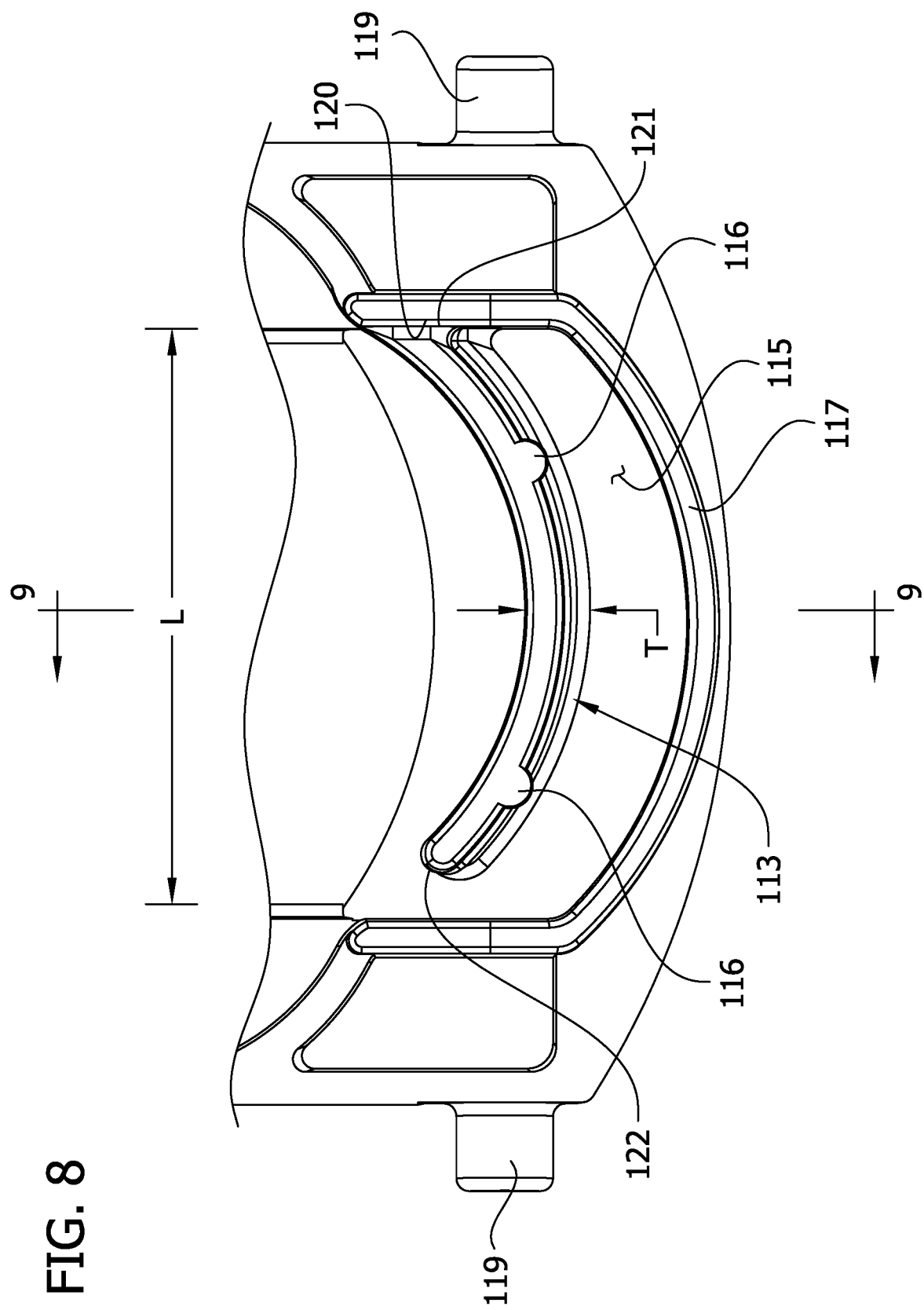
FIG. 8 is an enlarged fragmentary view of the cassette in FIG. 7 showing a stator member of the cassette.
Figure 9:
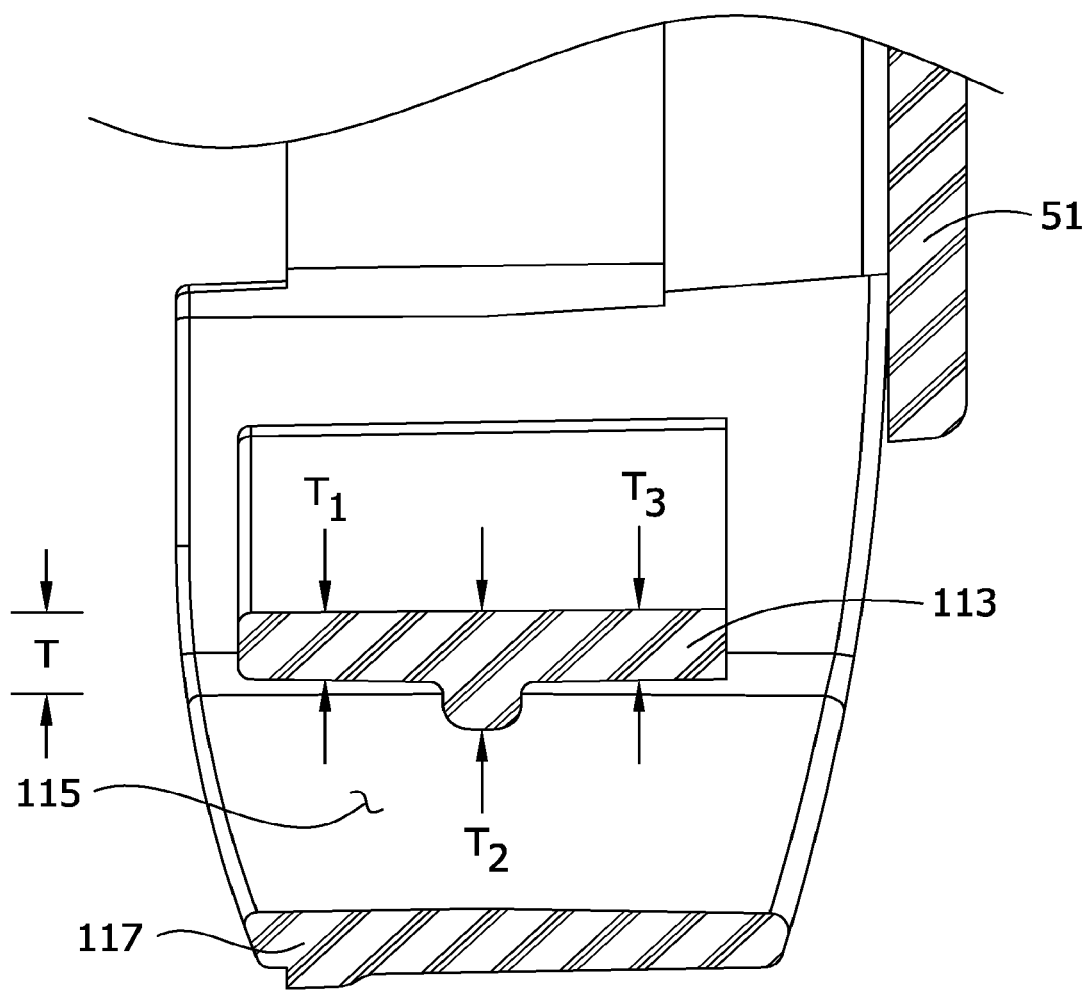
FIG. 9 is a sectional view of the stator member taken through line 9-9 in FIG. 8.

Referring to FIGS. 5 and 7, cutouts 85 may be formed in the top wall 63 of the cassette body 51 for receiving the second attachment portions 75, 81 of the inlet and outlet ports 69, 71 of the fitting 65. Locator walls 87 may extend vertically near the top of the cassette body 51. T-shaped guide walls 88 may extend from side walls 61 of the cassette body 51. An arched wall 89 may be disposed between the side walls 61 generally at a center of the cassette body 51. The base 67 of the fitting 65 rests on the pairs of upper and lower lateral locator walls 87A, 87B and the central locator wall 87C is received in a recess 90 in the base 67. The engagement between the central locator wall 87C and the recess 90 prevents or at least inhibits any lateral movement of the fitting 65 in the cassette 5. The horizontal portion of the arched wall 89 limits movement of the fitting 65 downward in the cassette 5. The first attachment portions 73, 79 of the fitting 65 are received between the T-shaped guide walls 88 and legs of the arched wall 89 that form guide channels for the respective, e.g., inlet and outlet, ends of the tube 45. The guide channels can be formed in other ways or completely omitted.

Figure 4:
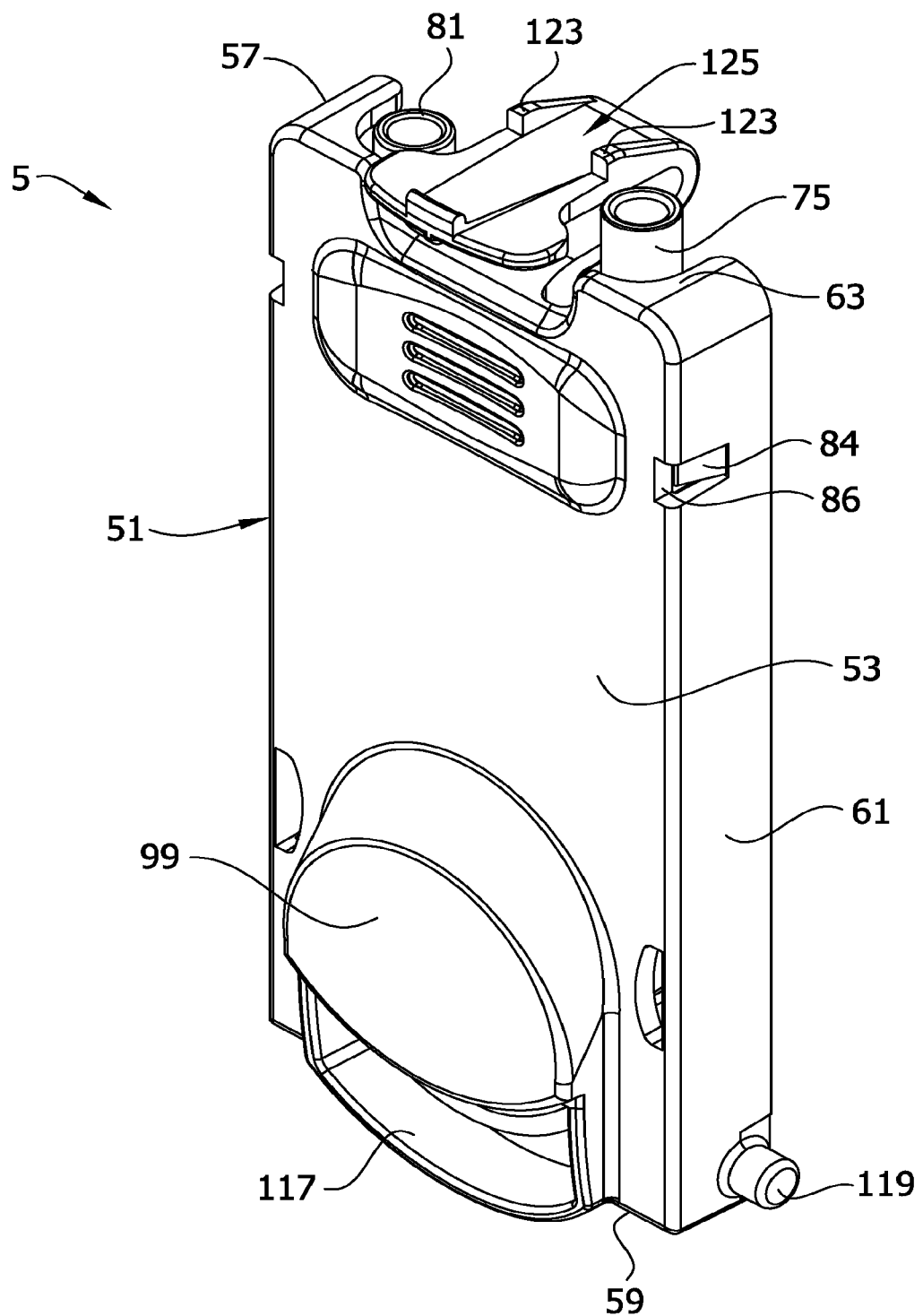
FIG. 4 is front perspective view of the cassette.

An arcuate wall 95 may be disposed generally at a middle of the cassette body 51 to define a rotor recess 97 for receiving at least a portion of the rotor 37 of the pump 1 when the cassette 5 is attached to the housing 3. The rotor recess 97 may form a bump-out 99 on the front 53 of the cassette body 51 (FIG. 4). Inlet and outlet outer curved guide walls 101 may extend generally parallel to opposite sides of arcuate wall 95. Inlet and outlet inner curved guide walls 103 may extend upward from the arcuate wall 95 generally parallel to the inlet and outlet outer curved guide walls 101, respectively, forming inlet and outlet openings for receiving respective inlet and outlet portions of the tube 45. The guide walls 101, 103 and arcuate wall 95 may form a tube channel for receiving a lower portion of the tube 45 in a looped configuration to properly position the tube relative to the rotor 37 when the cassette 5 is attached to the housing 3. The arcuate wall 95 and curved guide walls 101, 103 may receive the tube in close fitting relation around the sides of the rotor recess 97. Lips 100 may extend over the tube channel to hold the tube 45 in the tube channel and to retain the tube 45 in the cassette, constraining the tube according to a third axis. The outer curved guide walls 101 may terminate generally at a bottom side of the rotor recess 97 so that the tube 45 is not directly opposed by the guide walls 101, 103 or the arcuate wall 95 at the bottom of the rotor recess 97.

Figure 13:
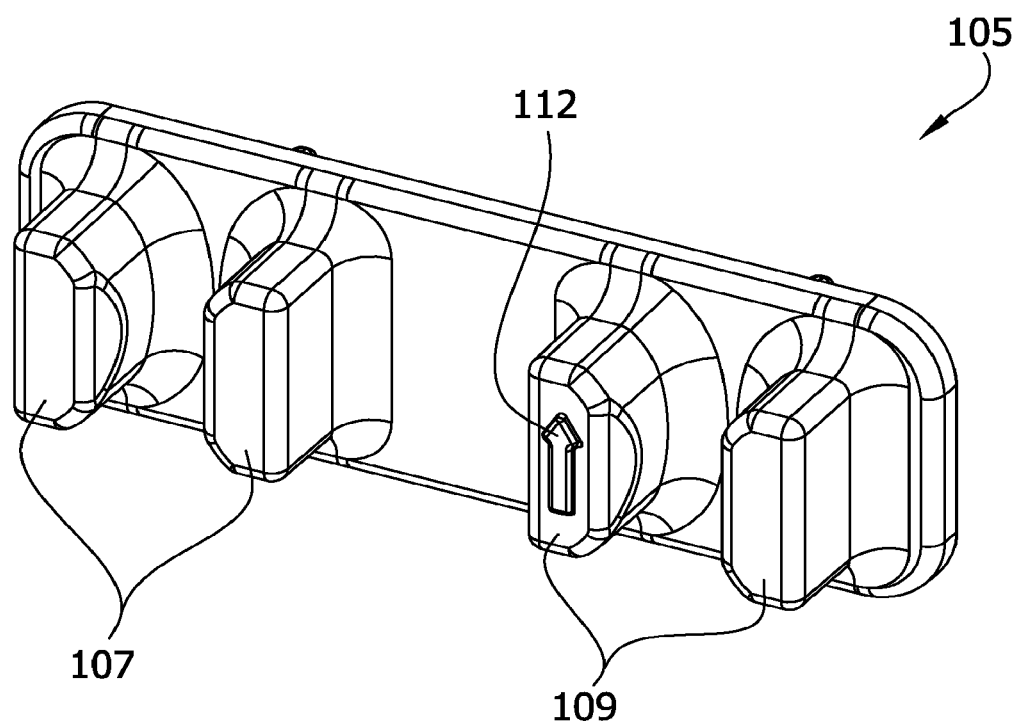
FIG. 13 is a perspective view of an insert of the pumping apparatus.
Figure 14:
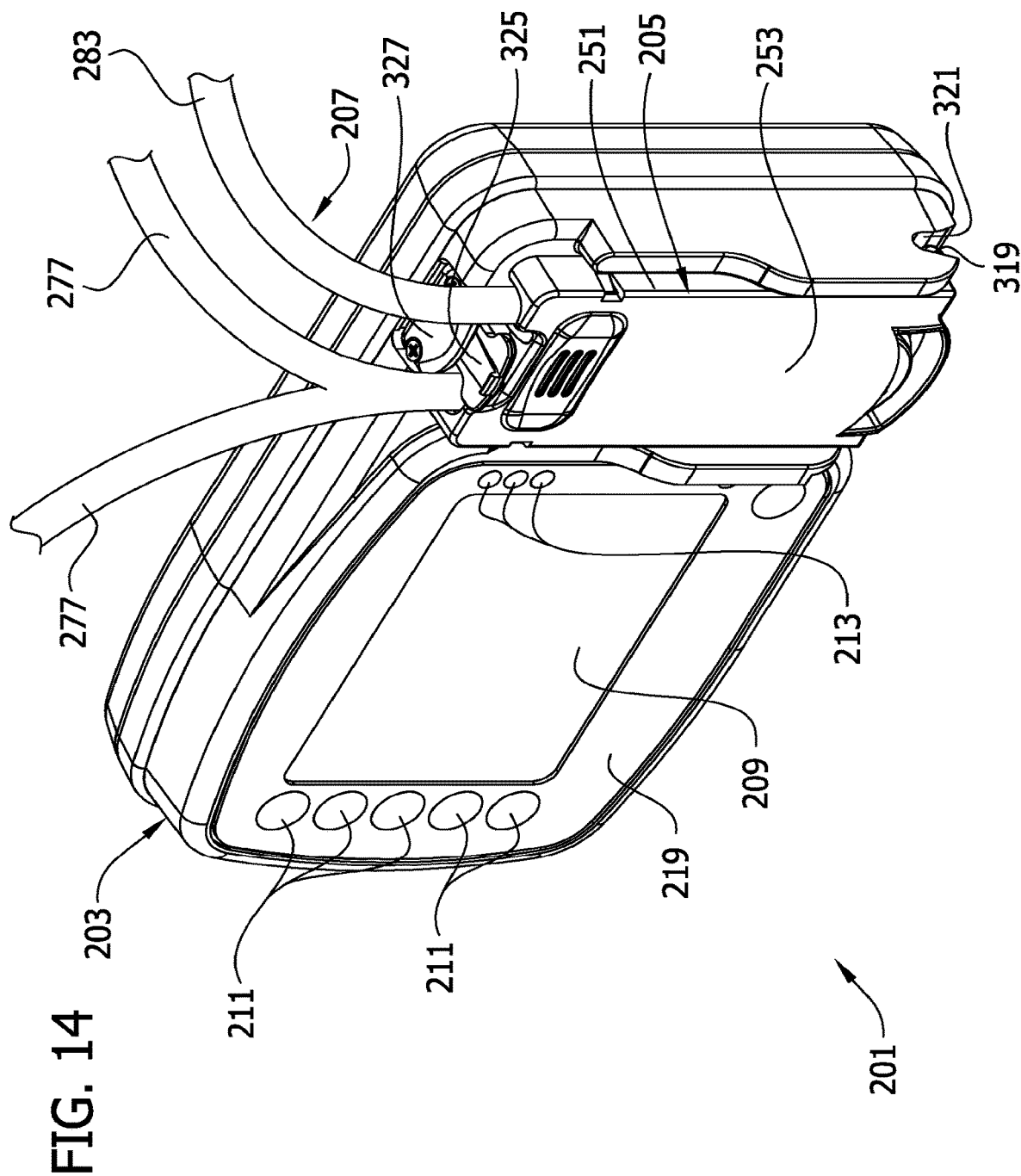
FIG. 14 is a perspective view of a pump system with a pump and a set and a cassette, in accordance with one or more further embodiments of the present invention.
Figure 15:
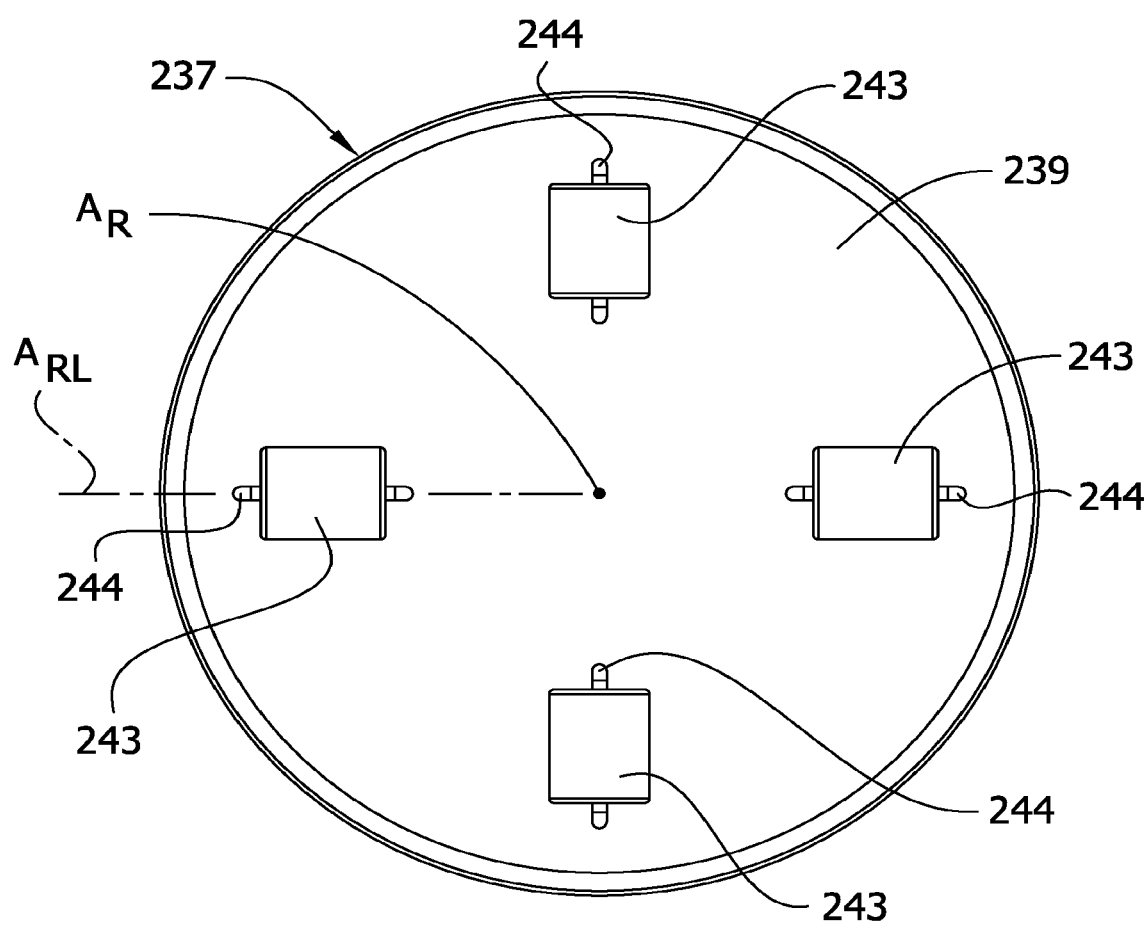
FIG. 15 is an elevation view a rotor with a roller of a pumping device of the pump, utilizable in the feeding system of FIG. 14.
Figure 16:
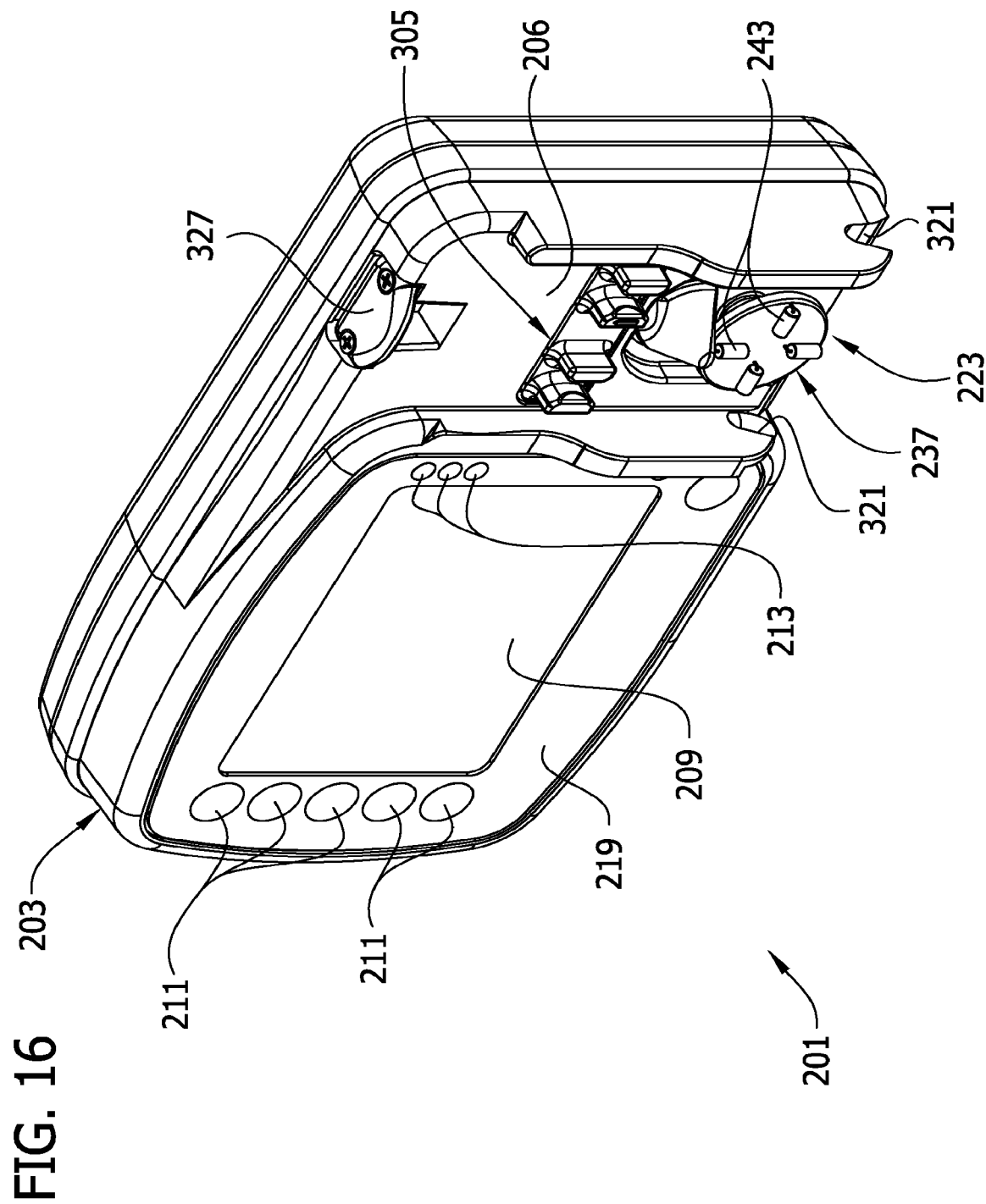
FIG. 16 is a perspective view of the pump of FIG. 15 with the cassette and set removed.
Figure 17:
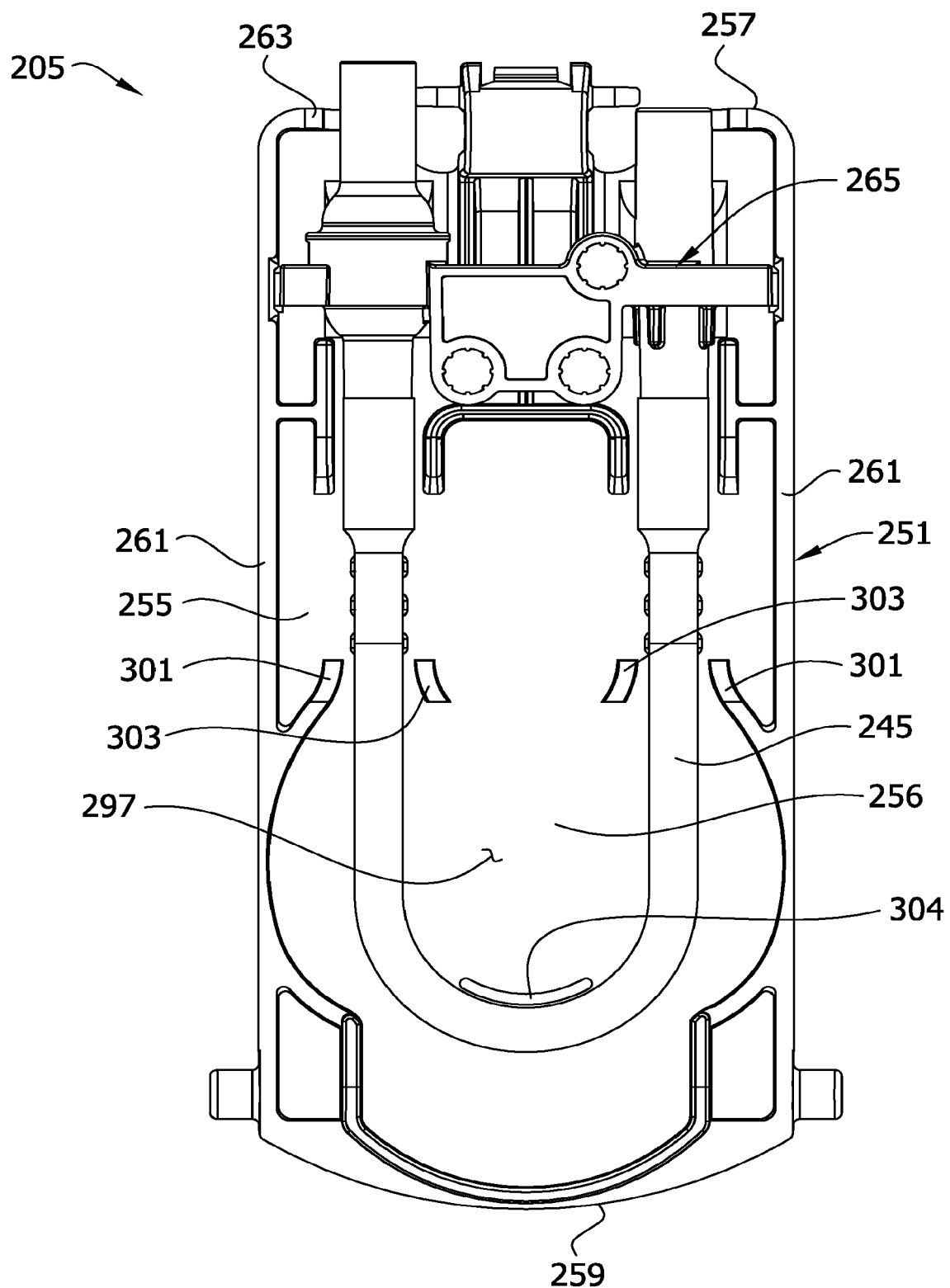
FIG. 17 is a rear elevation view of a cassette utilizable in the pump system of FIG. 14.
Figure 18:
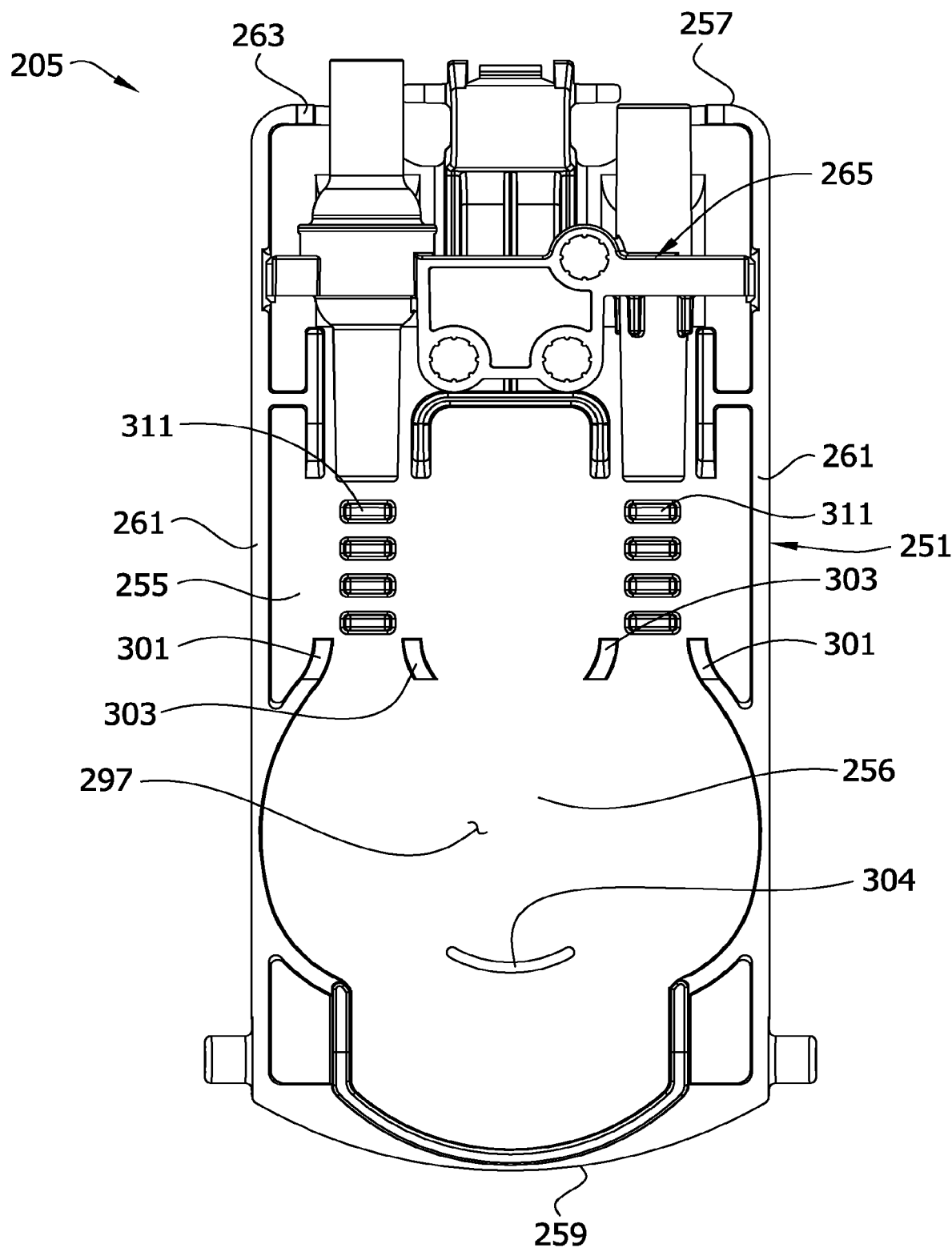
FIG. 18 is a rear elevation view of the cassette of FIG. 17 with a tube removed from the cassette.

An insert 105 may be received in the cassette recess 6 in the housing 3 to aid in securing the cassette 5 and tube 45 in the cassette recess 6 (FIGS. 3 and 13). The insert 105 may be positioned in the recess 6 such that the insert 105 is received in the back cavity of the cassette 5 between the T-shaped guide walls 88, arched wall 89, and the curved guide walls 101, 103 when the cassette 6 is attached to the housing 3. The insert 105 may comprise a pair of opposing first projections 107 disposed at an inlet side of the insert for receiving the inlet portion of the tube 45, and a pair of opposing second projections 109 disposed at an outlet side of the insert for receiving the outlet portion of the tube. Ribs 111 (FIG. 7) on the back 55 of the cassette body 51 may be positioned to engage the inlet and outlet portions of the tube 45 between the first and second projections 107, 109 to grip the inlet and outlet portions to aid in inserting the portions into the projections. Indicia 112 may be disposed on at least one of the second projections 109 indicating the direction of fluid flow in the tube 45. In the illustrated embodiment, the indicia 112 is in the form of an arrow.

Referring to FIGS. 5-9, a stator member 113 may be disposed a bottom portion of the cassette body 51 in a cavity such as stator opening 115 generally at or proximate the bottom of the rotor recess 97. Thus, when the cassette 5 is attached to the housing 3, the stator member 113 is typically positioned generally opposite a bottom of the rotor 37. In advantageous configurations, the stator member 113 may support the tube 45 of the feeding set 7 when the rollers 43 engage the tube, as explained below. In some cases, the stator member 113 may have an arcuate shape extending along a length L of the stator member. As in the exemplarily illustrated embodiments, the stator member 113 may be a cantilevered member anchored only at a first end 121 to the cassette body 51 and at least partially free to float in the stator opening 115 relative to the cassette body 51. As shown, the flexible stator member 113 may pivot about its connection or anchor 120 at the first end 121 to the remainder of the cassette 5 and may flatten out. For example, the stator member can have the first end 121 affixed to the cassette body and a second end 122 that is unfixed which can float or be displaced to allow a reaction segment having a surface of the stator member to have a deflection displacement. For example, as the at least one roller traverses along the tube while revolving about the axis of rotation of the rotor, the flexible stator member 113 may be displaced or deflect to a deflection displacement in reaction to the applied force by the one or more rollers 43 during revolution thereof about the axis of rotation. The deflection displacement can be defined as the maximum amount of translation of the second end of the stator. Variants of the invention may involve a flexible stator member 113 having an arcuate radius of curvature that is at about the radius of revolution of the rollers about the axis of rotation and may have a center of curvature C that is coincident on the axis of rotation. In some cases, the flexible stator member is a cantilever having one end secured to the cassette body with an arcuate reaction surface that has a variable radius of curvature. For example, the degree of curvature of the arcuate reaction surface can increase from the secured end to the free end; however, in other cases, degree of curvature of the arcuate reaction surface can decrease from the secured end to the free end. Thus, the flexible stator member can be an arcuate cantilevered member with no center of curvature. Further, the flexible stator member can be an arcuate cantilevered member with a center of curvature that is not coincident with the axis of rotation.

The flexible stator member 113 can have a flange on a second surface, opposite the arcuate surface of the reaction segment. For example, a width W (FIG. 9) of the flexible stator member 113 extends transverse to the length L, and a thickness T of the stator member may vary along the width of the stator member. As such, the flexible stator member 113 has a first section extending along the length L of the stator member having a thickness $T_1$ and a second section extending along the length of the stator member having a thickness $T_2$ that is greater than the thickness $T_1$ of the first section. A third section of the stator member has a thickness $T_3$ equal to the thickness $T_1$ of the first section. The increased thickness $T_2$ of the second section provides structural rigidity to the flexible stator member 113 to resist plastic deformation from repeated deformation due to engagement by the rollers 43. The increased thickness $T_2$ may be considered a longitudinal rib of the flexible stator member 113. Transverse ribs 116 on a bottom of the first section can provide structural rigidity to the flexible stator member 113 and can serve as contacting surfaces that facilitate removal, such as by ejection, of the cantilevered member from a mold cavity. In the illustrated embodiment, the first, second and third sections of the flexible stator member 113 are formed integrally. The stator member could be formed from three separate sections attached together in a suitable manner. In the illustrated embodiment, the flexible stator member 113 may be integrally formed as one piece with the cassette body 51. However, the flexible stator member 113 could be formed separately from the cassette body 51 and attached to the cassette body by a suitable means. For example, the flexible stator can have an elongate extension portion that is engaged into an engagement cavity in the cassette body wherein the engagement cavity is correspondingly sized and shaped to receive the extension portion. In this manner, a stator member can be selected from a plurality of candidates of differing mechanical characteristics, such as modulus, color, radius of curvature, to tailor the cassette operating parameters, with or without consideration for any of the tube characteristics, and provide specific flow performance attributes during pumping operation.

A stop member or stop 117 may be disposed at a bottom of the stator opening 115 to limit the floating movement of the flexible stator member 113 to a maximum displacement. The stop 117 may be spaced relative to the underside of the flexible stator member 113 to prevent flexing of the stator member that would result in plastic deformation of the stator member. For example, the stop member may be positioned to limit the magnitude of the deflection displacement distance of the unfixed end 122 to the maximum displacement. In the illustrated embodiment, the stop 117 is formed as part of the cassette body 51. However, the stop 117 could be formed separately from the cassette body 51 and attached to the cassette body in a suitable fashion. In other cases, stop 117 may be formed on the housing 3 and configured to limit the displacement of the flexible stator member 113 to the maximum displacement. The stop 117 may have a width W2 that is greater than the width W of the flexible stator member 113 so that the stop provides an adequate surface area to limit movement of the stator member. The stop 117 can serve to shield the flexible stator member 113 and is typically sized to prevent or reduce the likelihood of snagging or catching the member 113.

Prior to attaching the cassette 5 to the pump housing 3, the inlet and outlet tubing 77, 83 may be attached to the inlet and outlet ports 69, 71, respectively, of the cassette. To attach the cassette 5 the pump housing 3, one or more pins or raised projections 119 at the bottom 59 of the cassette body 51 may be inserted in slots 124 at the bottom of the recess 6 in the housing 3. The engagement between the raised projections 119 and slots 124 generally locates the cassette 5 on the housing 3. The cassette body 51 can then be rotated up until ledges 123 on a tab 125 at the top 57 of the cassette body are captured by a catch 127 at the top of the recess 6. In the illustrated embodiment, the raised projections 119 and ledges 123 are formed integrally with the cassette body 51. However, the raised projections 119 and ledges 123 can be formed separately from the cassette body 51 and attached to the cassette body in a suitable fashion. To detach the cassette 5 from the pump housing 3, the tab 125 can be depressed to disengage the ledges 123 from the catch 127.

In general, the volume of fluid in an aliquot can be determined by a calculation based on the size of the tube (i.e., inner diameter) and a length of a pinched off or isolated section of the tube between the rollers. In conventional pumps, adjacent rollers pinch and stretch the portion of the tube between the rollers. For instance, a portion of the tube on an inlet side of a roller may be placed in tension, and a portion of the tube on an outlet side of the roller may be placed in compression. This stretching and compressing changes the dimensions of the tube which alters the amount of fluid produced in each aliquot. Thus, the calculated amount of fluid in the aliquot will differ from the actual amount of fluid in the aliquot.

The pump 1 can produce an actual fluid flow consistent with the calculated fluid flow. Once the cassette 5 is attached to the pump housing 3, the tube 45 of the feeding set 7 is positioned for engagement by the rollers 43 of the pump 1. The rollers 43 engage the tube 45 at portions of the tube supported by the flexible stator member 113. Engagement of the tube 45 by a roller 43 causes the flexible stator member 113 to flex or move away from the roller. In contrast to conventional peristaltic pumps which achieves an aliquot by severely stretching the elastomeric tube, it is believed that the present invention advantageously facilitates creating aliquots by utilizing the flexible stator member in compressing the tube with the rollers which can accommodate the use of tubes with thicker wall dimensions which in turn can improve tube resiliency and accommodate greater applied forces with consequent tube longevity because of greater degradation resistance associated with thicker tube walls. In particular, the movement allows the tube 45 to at least partially straighten out into a more linear configuration permitting the rollers 43 to occlude the tube in a semi linear fashion. Therefore, instead of pulling and stretching the tube 45 as can be the case with rollers in conventional pumps, the rollers 43 slide along the tube and occlude the tube in a reduced tension state. As a result, the rollers 43 produce aliquots consistent with the actual linear dimensions of the tube 45. Accordingly, the calculated aliquot volume of the pump 1 more closely matches the actual aliquot volume produced by the pump resulting in more accurate feeding.

It will be understood that occlusion of the tube 45 caused by the roller 43 pinching off the lumen 45 against the flexible stator member 113 will result in a nominal amount of local tension and compression on the tube at the point of occlusion. However, the nominal tension and compression produced by occlusion does not meaningfully alter the volume in the tube from which the pump 1 calculates the amount of fluid or aliquot being delivered to the subject.

Because the flexible stator member 113 may be formed from plastic and free to flex in response to engagement by the rollers 43, the stator member could be susceptible to plastic deformation. To reduce any chance of a "free flow" condition, the stop 117 is positioned below the flexible stator member 113 to limit the distance the stator member can flex so that the stator member cannot be plastically deformed such that the "free flow" condition is created. Therefore, the stop 117 can ensure that the flexible stator member 113 moves a distance to compensate for tolerance differences between the rotor rollers and the reaction surface but sufficiently so that the rollers cannot occlude the tube to form aliquots of fluid to be pumped through the feeding set 7. The stop can further prevent the stator member from being undesirably caught or impinged.

The pump 1 may also be provided with a detection system for detecting the position of the stator member, the tube 45 or the cassette 5. The detection feature can be used to ensure the flexible stator member 113 is properly positioned against the rotor preventing "free flow" while the cassette 5 is being loaded on the pump housing 3. Thus, the detection feature may function as a failsafe to ensure the tube 45 is properly occluded by the rollers 43 and flexible stator member 113 before pumping is initiated. A preferred detection method may use visible and infrared light emitters on the pump 1 to shine light against a reflective surface (not shown) on the cassette 5 for detection by detectors on the pump. This can be used to prevent against false positives that could occur with other detection methods that use only IR or visible light sensors. A keyed configuration (not shown) on the flexible stator member 113 can also be used in addition to the visible light and infrared emitters/detectors as a backup up to verify the reading from the emitters/detectors. The guide walls 91, 101, 103 may also position the tube 45 in place between the emitters/detectors for detection to ensure the tube is properly received in the cassette 5. In accordance with further embodiments, positive acknowledging engagement of the cassette in the pump can be effected by detecting a magnetic field of a magnetic material disposed in the flexible stator member. In some cases, the pump can have an interlock circuit coupled to a sensor that measures Hall Effect phenomena associated with current generated by a magnetic field created by oscillating the magnetic material in the flexible stator member when the tube is periodically pinched by the rollers of the rotating rotors. For example, the magnetic material can be disposed at or proximate the end 122 of the flexible stator member. During operation, the flexible stator member will typically have an oscillating displacement as the rollers, during revolution around the axis of rotation, traverse on and pinch the tube against the reaction surface which manifests into the oscillating displacement. The magnetic material at the oscillating end 122 creates a variable magnetic field which creates induces a change in current in a Hall Effect sensor, which is typically disposed on the housing 3. Any deviation from an expected current from the Hall Effect sensor can be an indication of failure of the pump or components thereof. Thus, monitoring oscillating magnetic field can be used to terminate the pump and can trigger an alarm.

Referring to FIGS. 14-19, a second embodiment of peristaltic pump is generally indicated at 201. The pump of the second embodiment is similar to the pump 1 of the first embodiment. Accordingly, parts of the pump 201 generally corresponding to those of the pump 1 will be given the same number, plus "200." The pump 201 may comprise a housing generally indicated at 203 that is constructed so as to mount a cassette, generally indicated at 205, and a feeding set (broadly, a "pump set"), a fragmentary portion generally indicated at 207, removably received in the cassette. The cassette 205 is releasably attachable to the housing 203. In the illustrated embodiment, the cassette 205 is removably received in a cassette recess 206 in the housing 203.

The pump 201 may further include a pumping unit indicated generally at 223 comprising a pump motor (not shown) connected to a rotor shaft (not shown). A rotor (generally indicated at 237) may be mounted on the rotor shaft of the pumping unit 223. The rotor 237 may include a disk 239 and rollers 243 mounted on the disk for rotation relative to the disk about their longitudinal axes. In the illustrated embodiment, four rollers 243 are shown. It will be understood that a different number of rollers 243 may be mounted on the disk 239. The motor rotates the rotor 237 about a rotor axis $A_R$. The rollers 243 may be mounted on a face of the rotor 237 by pins 244 such that each roller rotates on the pins about a roller axis $A_{RL}$ that extends generally perpendicular to the rotor axis $A_R$. This is contrary to conventional pumps where the rollers are mounted on the rotor such that the rollers rotate about an axis that is parallel to the rotor axis. As will be explained in greater detail below, this configuration allows the feeding set 207 to be mounted in the housing 203 in a non-stretched configuration such that the feeding set is not placed in tension by the rollers 243 upon loading of the feeding set on the pump. The rollers 243 are configured to engage a tube 245 of the feeding set 207 to deliver fluid through the feeding set to a subject when the feeding set is received in cassette 205 and the cassette is attached to the pump housing 203.

The cassette 205 may comprise a cassette body 251 having a front 253, a back 255, a top 257 and a bottom 259. Side walls 261 and top wall 263 may extend from the back 255 of the cassette body 251 forming a back cavity configured for receiving a fitting 265. The back 255 of the cassette 205 may define a stator surface 256. The stator surface may extend generally parallel to the rotor disk 239 and generally perpendicular to rotor axis $A_R$ when the cassette 205 is attached to the housing 203. In a preferred embodiment, the stator surface 256 is planar providing a flat surface for occluding the tube 245.

The bottom of the back cavity of the cassette 205 defines a rotor recess 297. Inlet and outlet outer curved guide walls 301 and respective inlet and outlet inner curved guide walls 303 may extend generally parallel to each other forming inlet and outlet openings for receiving respective inlet and outlet portions of the tube 245. A bottom curved guide wall 304 may be disposed at a bottom of the rotor recess 297. Additional guide walls may be utilized to facilitate the alignment of the tube on the corresponding orbital path of the rollers 243 about the axis $A_R$. The guide walls 301, 303, 304 may form a tube channel for receiving a lower portion of the tube 245 in a looped configuration to properly position the tube relative to the rotor 237 when the cassette 205 is attached to the housing 203. The curved guide walls 301, 303, 304 receive the tube in close relation around the sides of the rotor recess 297.

Figure 19:
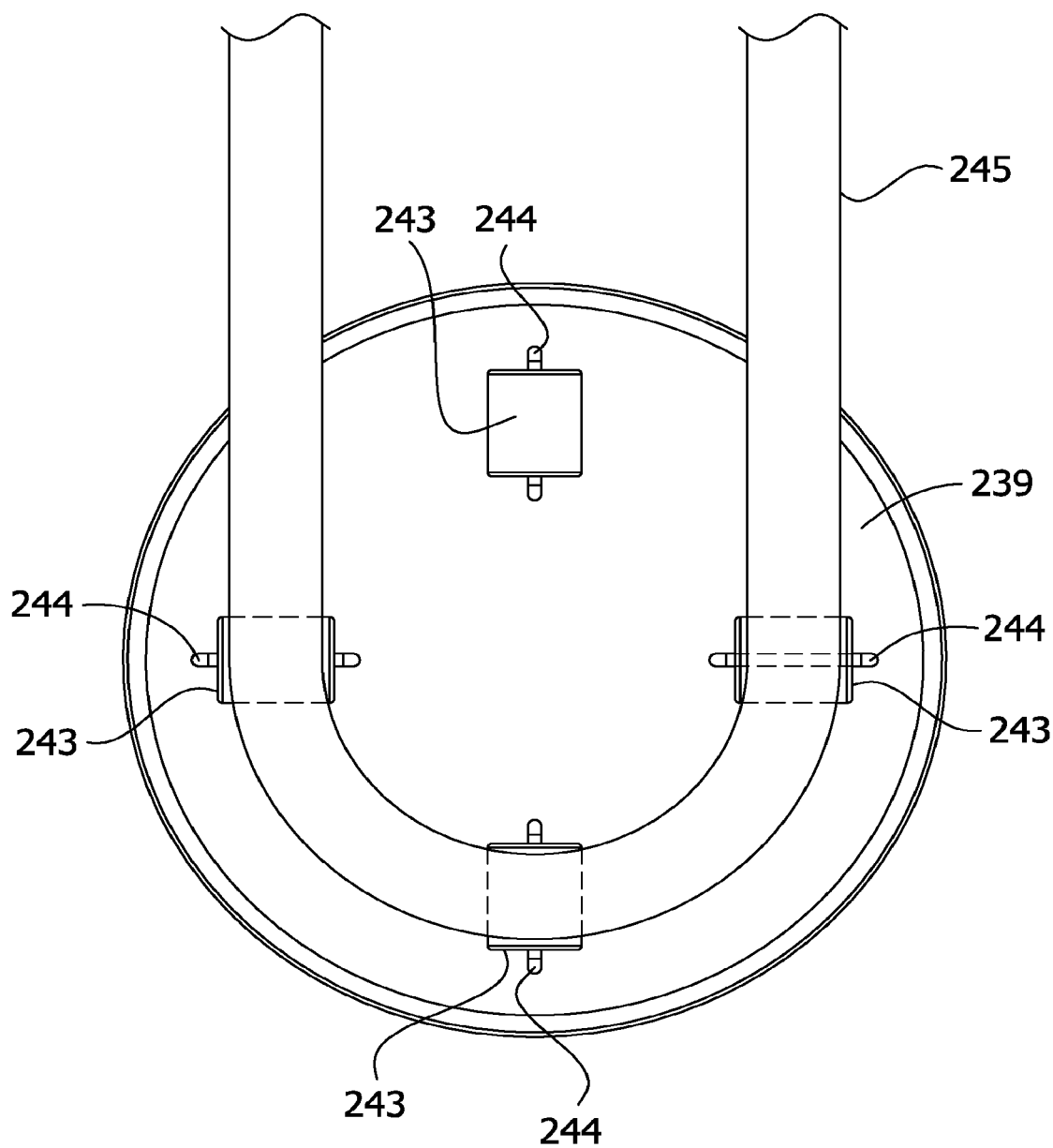
FIG. 19 is a schematic view of the tube and the rotor of FIG. 15 engaged by rollers (in phantom).

The feeding set 207 can thus be mounted on the pump 201 in a non-stretched configuration so that the actual flow of fluid through the feeding set is more consistent with the calculated fluid flow over the life of the feeding set. Once the cassette 205 is attached to the pump housing 203, the tube 245 of the feeding set 207 is positioned for engagement by the rollers 243 of the pump 201 (FIG. 19). The rollers 243 rotate on the rotor 237 and occlude the tube 245 by compressing the tube between the rollers and the stator surface 256. The guide walls 301, 303, 304 are positioned such that they do not interfere with the path of the rollers 243 so that the rollers may properly occlude the tube 245. Because the tube 245 is not stretched around the rollers 243 as in conventional designs, the tube is positioned in a relaxed, non-stretched state. Therefore, the volume of fluid in each aliquot is consistent with the calculated volume of fluid based on the size of the tube. Accordingly, the pump 201 is capable of producing a more accurate feeding than conventional pumps.

Having described the invention in detail, it will be apparent that modifications and variations are possible without departing from the scope of the invention defined in the appended claims. For example, the cassette 205 can have a cantilevered stator surface as a stator member by having an affixed edge portion thereof proximate the guide walls 303 and an unfixed edge portion, opposite the affixed portion, proximate the guide wall 304 and proximate along or around an orbital path of the rollers. The unfixed edge portion can be disposed at a separation distance from the rollers, or the rotor, that is less than a spacing between the fixed edge portion and the rotor. Thus, for example, the cantilevered surface can be canted or inclined relative to a plane defined by the rotor or the orbital path of the rollers. In other modifications, the peristaltic pump can have an integrally formed cantilevered reaction member disposed to provide support a flexible tubing during deformation thereof by rollers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

The invention claimed is:

1. A pump set for use with a pumping apparatus having a rotor with a plurality of rollers mounted on the rotor rotatable about an axis of rotation, the pump set comprising:
   a cassette body having a top, a bottom, sides, and a center defined by a point midway between the top and the bottom and midway between the sides, the cassette body comprising a flexible stator with a fixed end secured to the cassette body at a connection, a second end opposite the fixed end, a middle portion including a reaction surface and a second surface opposite the reaction surface, the middle portion defined between the fixed end and the second end, the second end being free from any structure of the cassette body aside from the middle portion, the flexible stator having an arcuate shape curving inwards relative to the center of the cassette body; and
   a deformable tube secured to the cassette body, at least a portion of the deformable tube configured to be disposed against the reaction surface, the flexible stator being arranged in the cassette body to permit the flexible stator to float in the cassette body as the plurality of rollers traverse the deformable tube over a length of the reaction surface of the flexible stator, the flexible stator being constructed to pivot about the connection to the cassette body and flatten out upon engagement of the deformable tube by the plurality of rollers of the rotor during rotation of the rotor to deliver fluid through the deformable tube, wherein a section of the flexible stator extends along an entire length of the flexible stator from the fixed end to the second end, a width of the section extending partially across the flexible stator, and a thickness of the section extending from the reaction surface to the second surface, the thickness being constant along the entire length of the section.

2. The pump set as set forth in claim 1, wherein at least a portion of the reaction surface defines an arcuate surface with the center of curvature being coincident with the axis of rotation.

3. The pump set as set forth in claim 1, wherein the flexible stator is cantilevered at the fixed end and unfixed at the second end and the reaction surface has a deflection displacement.

4. The pump set as set forth in claim 3, further comprising an arcuate stop member constructed and arranged to limit the deflection displacement.

5. The pump set as set forth in claim 1, wherein the deformable tube is contained within the cassette body.

6. The pump set as set forth in claim 1, wherein the flexible stator further comprises a flange on the second surface, the flange extending along at least a portion of the second surface between the fixed end and the second end.

7. The pump set as set forth in claim 1, wherein the deformable tube is disposed in the cassette in a U-shape and the flexible stator opposes an outer arcuate portion of the U-shape.

8. The pump set as set forth in claim 1, wherein the deformable tube is disposed in the cassette in a U-shape and the flexible stator opposes the deformable tube at a base of the U-shape.

9. A pump set for use with a pumping apparatus having a rotor with at least one roller mounted on the rotor rotatable about an axis of rotation, the pump set comprising:
a cassette body including a flexible stator with a fixed end secured to the cassette body at a connection, a second end opposite the fixed end, a middle portion including a reaction surface and a second surface opposite the reaction surface, the middle portion defined between the fixed end and the second end, the second end being free from any structure of the cassette body aside from the middle portion, the flexible stator having an arcuate shape curving relative to a center of the cassette body; and a deformable tube secured to the cassette body, at least a portion of the deformable tube configured to be disposed against the reaction surface, the flexible stator being arranged in the cassette body to permit the flexible stator to float in the cassette body as the at least one roller traverses the deformable tube over a length of the reaction surface of the flexible stator, the flexible stator constructed to pivot about the connection to the cassette body and flatten out upon engagement of the deformable tube by the at least one roller during rotation of the rotor to deliver fluid through the deformable tube, wherein the cassette body includes an arcuate wall opposing the reaction surface of the flexible stator such that the arcuate wall and the reaction surface form a cavity to receive the rotor therein, the resiliently deformable tube passing through the cavity between the arcuate wall and the flexible stator.

10. A pump set for use with a pumping apparatus, the pump set comprising:
a cassette including a flexible stator with a fixed end cantilevered to the cassette, a second end opposite the fixed end, and an arcuate portion extending along an entire length of the stator between the fixed end and the second end; and a resiliently deformable tube coupled to the cassette, at least a portion of the resiliently deformable tube configured to contact the arcuate portion;

wherein the flexible stator is configured to pivot about the fixed end and the arcuate portion is configured to displace upon engagement by a rotor of the pumping apparatus; and wherein the arcuate portion of the flexible stator includes a constant thickness between from the fixed end and to the second end.

11. The pump set as set forth in claim 10, wherein the flexible stator flattens upon engagement of the resiliently deformable tube by a roller of the rotor during rotation of the rotor to deliver fluid through the resiliently deformable tube.

12. The pump set as set forth in claim 11, wherein the flexible stator is arranged in the cassette to permit the flexible stator to float in the cassette as the roller traverses the resiliently deformable tube over a reaction surface of the flexible stator.

13. The pump set as set forth in claim 11, wherein the arcuate portion opposes the roller.

14. The pump set as set forth in claim 10, wherein the resiliently deformable tube is disposed in the cassette in a U-shape and the flexible stator opposes an outer arcuate portion of the U-shape.

* * * * *